(12) United States Patent
Parce et al.

(10) Patent No.: US 6,613,513 B1
(45) Date of Patent: Sep. 2, 2003

(54) SEQUENCING BY INCORPORATION

(75) Inventors: J. Wallace Parce, Palo Alto, CA (US); Theo T. Nikiforov, San Jose, CA (US); Tammy Burd Mehta, San Jose, CA (US); Anne R. Kopf-Sill, Portola Valley, CA (US); Andrea W. Chow, Los Altos, CA (US); Michael R. Knapp, Redwood City, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/510,205

(22) Filed: Feb. 22, 2000

Related U.S. Application Data

(60) Provisional application No. 60/121,223, filed on Feb. 23, 1999, provisional application No. 60/127,825, filed on Apr. 5, 1999, and provisional application No. 60/128,643, filed on Apr. 9, 1999.

(51) Int. Cl.[7] .......................... C12Q 1/68; C12P 19/34; G01N 33/00; C07H 21/02; C07H 21/04
(52) U.S. Cl. .................. 435/6; 435/91.1; 435/91.2; 436/94; 536/23.1; 536/24.3; 536/24.33
(58) Field of Search ................ 435/6, 7.1, 91.1, 435/91.2, 183, 283.1, 287.1, 287.2, 288.7; 536/26.6, 23.1, 24.3, 24.33, 25.32; 436/94; 422/80, 68.1, 82.05, 82.08

(56) References Cited

U.S. PATENT DOCUMENTS

| | | | |
|---|---|---|---|
| 4,390,403 A | 6/1983 | Batchelder |
| 4,863,849 A | 9/1989 | Malemede |
| 4,908,112 A | 3/1990 | Pace |

(List continued on next page.)

FOREIGN PATENT DOCUMENTS

| | | |
|---|---|---|
| EP | 0376611 A2 | 7/1990 |
| EP | 0620432 | 10/1994 |
| JP | 10-53099 | 3/1998 |
| WO | WO 90/13666 | 11/1990 |
| WO | WO 93/21340 | 10/1993 |
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO98/33939 * | 6/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56505 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/31495 | 6/1999 |
| WO | WO 99/34205 | 7/1999 |
| WO | WO 99/43432 | 9/1999 |
| WO | WO 99/44217 | 9/1999 |
| WO | WO 99/56954 | 11/1999 |
| WO | WO 00/09753 | 2/2000 |

OTHER PUBLICATIONS

Beskin et al. (1995) "On the mechanism of the modular primer effect" Nucleic Acids Research 23 (15):2881–2885.

Bousse et al. (1998) "Parallelism in integrated fluidic circuits," SPIE 3259:179–186.

Brenner, S. et al. (2000) "Gene expression analysis by massively parallel signature sequencing (MPSS) on microbead arrays". Nature Biotechnology (18) 630–634.

Bruchez et al. (1998) "Semiconductor Nanocrystals as Fluorescent Biological Labels" Science, 281: 2013–2016.

Bult et al. (1996) "Complete Genome Sequence of the Methanogenic Archaeon, *Methanococcus jannaschii*" Science 273:1058–1073.

Chee et al (1996) "Accessing Genetic Information with High–Density DNA Arrays" *Science* 274:610–614.

Chou, Hou–Pu et al. (1999) "A microfabricated device for sizing and sorting DNA molecules", Proc. Natl. Acad. Sci vol. 26 pp 11–13.

Coutlee et al. (1989) "Nonisoltopic Detection of RNA in an Enzyme Immunoassay Using a Monoclonal Antibody against DNA–RNA Hybrids" Analytical Biochemistry 181:153–162.

Drmanac et al. (1998) "Accurate sequencing by hybridization for DNA diagnostics and individual genomics." *Nature Biotechnology* 16:54–58.

(List continued on next page.)

*Primary Examiner*—Ethan Whisenant
*Assistant Examiner*—Frank Lu
(74) *Attorney, Agent, or Firm*—Quine Intellectual Property Law Group, P.C.; Stacy Landry; Gary Baker

(57) ABSTRACT

Nucleotides and nucleotide analogs are used in various sequencing by incorporation/sequencing by synthesis methods. Nucleotide analogs comprising 3'-blocking groups are used to provide reversible chain-termination for sequencing by synthesis. Typical blocking groups include phosphate groups and carbamate groups. Fluorescent nucleotides are used to perform sequencing by synthesis with detection by incorporation of the fluorescently labeled nucleotide, optionally followed by photobleaching and intercalating dyes are used to detect addition of a non-labeled nucleotide in sequencing by synthesis with detection by intercalation. Microfluidic devices, including particle arrays, are used in the sequencing methods.

26 Claims, 8 Drawing Sheets

U.S. PATENT DOCUMENTS

| | | |
|---|---|---|
| 4,971,903 A | 11/1990 | Hyman |
| 5,122,614 A | 6/1992 | Zalipsky |
| 5,126,022 A | 6/1992 | Soane et al. |
| 5,187,085 A | 2/1993 | Lee et al. |
| 5,202,231 A | 4/1993 | Drmanac et al. |
| 5,302,509 A | 4/1994 | Cheeseman |
| 5,332,666 A | 7/1994 | Prober et al. |
| 5,498,392 A | 3/1996 | Wilding et al. |
| 5,525,711 A | 6/1996 | Hawkins et al. |
| 5,571,410 A | 11/1996 | Swedberg et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,650,234 A | 7/1997 | Dolence et al. |
| 5,653,939 A | 8/1997 | Hollis et al. |
| 5,699,157 A | 12/1997 | Parce |
| 5,719,060 A | 2/1998 | Hutchens et al. |
| 5,747,349 A | 5/1998 | van den Engh et al. |
| 5,750,015 A | 5/1998 | Soane et al. |
| 5,779,868 A | 7/1998 | Parce et al. |
| 5,798,210 A | 8/1998 | Canard |
| 5,800,690 A | 9/1998 | Chow et al. |
| 5,842,787 A | 12/1998 | Kopf-Sill et al. |
| 5,852,495 A | 12/1998 | Parce |
| 5,856,174 A | 1/1999 | Lipshutz et al. |
| 5,863,502 A | 1/1999 | Southgate et al. |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,942,443 A | 8/1999 | Parce et al. |
| 5,948,227 A | 9/1999 | Dubrow |
| 5,955,028 A | 9/1999 | Chow |
| 5,957,579 A | 9/1999 | Kopf-Sill et al. |
| 5,958,203 A | 9/1999 | Parce et al. |
| 5,958,694 A | 9/1999 | Nikiforov |
| 5,959,291 A | 9/1999 | Jensen |
| 5,964,995 A | 10/1999 | Nikiforov et al. |
| 5,965,001 A | 10/1999 | Chow et al. |
| 5,965,410 A | 10/1999 | Chow et al. |
| 5,972,187 A | 10/1999 | Parce et al. |
| 5,976,336 A | 11/1999 | Dubrow et al. |
| 5,989,402 A | 11/1999 | Chow et al. |
| 6,001,231 A | 12/1999 | Kopf-Sill |
| 6,004,515 A | 12/1999 | Parce et al. |
| 6,011,252 A | 1/2000 | Jensen |
| 6,012,902 A | 1/2000 | Parce |
| 6,042,710 A | 3/2000 | Dubrow |
| 6,046,056 A | 4/2000 | Parce et al. |
| 6,136,543 A * | 10/2000 | Anazawa et al. |
| 6,288,220 B1 | 9/2001 | Kambara et al. |

OTHER PUBLICATIONS

Drmanac et al., (1989) "Sequencing of Megabase Plus DNA by Hybridization: Theory of the Method" *Genomics* 4:114–128.

Eckstein et al. "Phosphorothioates in molecular biology" Trends in Biochem 14: 97 (1989).

Effenhauser et al. (1993) Glass Chips for High–Speed Capillary Electrophoresis Separations with Submicrometer Plate Heights Anal. Chem 65:2637–2642.

Effenhauser et al. (1994) High–Speed Separation of Antisense Oligonucleotides on a Micromachined Capillary Electrophoresis Device. Anal. Chem. 66:2949–2953.

Fan and Harrison (1994) Micromachining of Capillary Electrophoresis Injectors and Separators on Glass Chips and Evaluation of Flow at Capillary Intersection. Anal.Chem. 66:177–184.

Fleischmann et al. (1995) Science 269:496–512.

Fodor et al. (1991) "Light–Directed, Spatially Addressable Parallel Chemical Synthesis" Science, 251; 767–777.

Fodor (1997) "Genes, chips and the Human Genome" *FASEB Journal* 11:121–121.

Fodor (1997) "Massively Parallel Genomics" *Science.* 277: 393–395.

Fraser et al. (1995) "The Minimal Gene Complement of Mycoplasma genitalium" Science 270: 397–403.

Gay et al. J. Chem. Soc. 8:1123 (1970).

Harris, J. Milton "Laboratory Synthesis of Polyethylene Glycol Derivatives" Rev. Macromol. Chem. Phys., C25(3), 325–373 (1985).

Harrison, et al. (1992) Capillary Electrophoresis and Sample Injection Systems Integrated on a Planar Glass Chip Anal. Chem. 64:1926–1932.

Harrison, et al. (1993) Micromachining a Miniaturized Capillary Electrophoresis–Based Chemical Analysis System on a Chip. Science 261:895–897.

Harrison and Glavania (1993) "Towards Miniaturized Electrophoresis and Chemical System Analysis Systems on Silicon: An Alternative to Chemical Sensors." Sensors and Actuators 10:107–116.

Ishii & Ghosh (1993) "Bead–Based Sandwich Hybridization Characteristics of Oligonucleotide–Alkaline Phosphatase Conjugates and Their Potential for Quantitating Target RNA Sequences" Bioconjugate chem. American Chemical Society 4:34–41.

Jacobson et al. (1994) "Open Channel Electrochromatography on a Microchip" Anal. Chem. 66:2369–2373.

Jacobson et al. (1994) "Precolumn Reactions with Electrophoretic Analysis Integrated on Microchip" Anal. Chem. 66:4127–4132.

Jacobson et al. (1994) "Effects of Injection Schemes and Column Geometry on the Performance of Microchip Electrophoresis Devices" Anal. Chem. 66:1107–1113.

Jacobson et al. (1994) High Speed Separations on a Microchip. Anal. Chem. 66:1114–1118.

Jacobson and Ramsey (1995) "Microchip electrophoresis with sample stacking" Electrophoresis 16:481–486.

Kopf–Sill et al. (1997) "Complexity and performance of on–chip biochemical assays," SPIE 2978:172–179 Feb. 10–11.

Mathe, C. et al. (1998) "Phosphopeptide Prodrug Bearing an S–Acyl-2thoethyl Enzyme–Labile Phosphate Protection" J.Org. Chem. 63: 8547–8550 (1998).

Nie and Chan (1998) "Quantum Dot Bioconjugates for Ultrasensitive Nonisotopic Detection" Science 281:2016–2018.

Nyren, et al (1993) "Solid Phase DNA Minisequencing by an Enzymatic Luminometric Inorganic Pyrophosphate Detection Assay," Anal. Biochem. 208:171–175.

Ronaghi, Mostafa et al. (1996) "Real–Time DNA Sequencing Using Detection of Pyrophosphate Release" Anal. Biochem. 242:84–89.

Porter et al. (1997)"Direct PCR sequencing with boronated nucleotides" Nucleic Acids Research 25 (8): 1611–1617.

Raja et al. (1997) "DNA sequencing using differential extension with nucleotide subsets (DENS)" Nucleic Acids Research 25 (4):800–805.

Rich et al. (1975) "Preparation of a New o–Nitrobenzyl Resin for Solid–Phase Synthesis of tert–Butyloxycarbonyl–Protected Peptide Acids" J. Am. Chem. Soc. 97:1575–1579.

Ronaghi et al. (1998) "A Sequencing Method Based on Real Time Pyrophosphate" Science 281:363–364.

Sanger et al. (1977) "DNA Sequencing with chain–terminating inhibitors" Proc. Nat. Acad. Sci., USA 74:5463–5467.

Seiler, et al. (1994) "Micromachining a Miniaturized Capillary Electrophoresis–Based Chemical Analysis System on a Chip" Mit Gebiete Lebensm. Hyg. 85:59–68.

Tomb et al. (1997) "The complete genome sequence of the gastric pathogen Helicobacter pylori" Nature 539–547.

Tyagi, S. "Taking a census of mRNA populations with microbeads", Nature. 18: Jun. 2000 597–598.

Wang, (1976) Solid Phase Synthesis of Protected Peptides via photolytic Cleavage of the α–Methylphenacyl Ester Anchoring Linkage J. Org. Chem. 41:3258.

Zalipsky et al, (1983) "Attachment of Drugs to Polyethylene Glycols" Eur. Polym. J., 19(12), 1177–1183.

Cohen, C.B. et al., "A Microchip–Based Enzyme Assay for Protein Kinase A," Anal. Chem. (1999) 273:89–97.

Dasgupta, P.K. et al., "Electroosmosis: A Reliable Fluid Propulsion System for Flow Injection Analysis," Anal. Chem. (1994) 66:1792–1798.

Jacobson, S.C. et al., "Fused Quartz Substrates for Microchip Electrophoresis," Anal. Chem. (1995) 67:2059–2063.

Manz, A. et al., "Electroosmotic pumping and electrophoretic separations for miniaturized chemical analysis systems," J. Micromech. Microeng. (1994) 4:257–265.

Ramsey, J.M. et al., "Microfabricated chemical measurement systems," Nature Med. (1995) 1:1093–1096.

Seiler, K. et al., "Planar Glass Chips for Capillary Electrophoresis: Repetitive Sample Injection, Quantitation, and Separation Efficiency," Anal. Chem. (1993) 65:1481–1488.

Seiler, K. et al., "Electroosmotic Pumping and Valveless Control of Fluid Flow Within a Manifold of Capillaries on a Glass Chip," Anal. Chem. (1994) 66:3485–3491.

Sundberg, S.A., "High–throughput and ultra–high–throughput screening: solution—and cell–based approches," Current Opinions in Biotechnology 2000, 11:47–53.

* cited by examiner

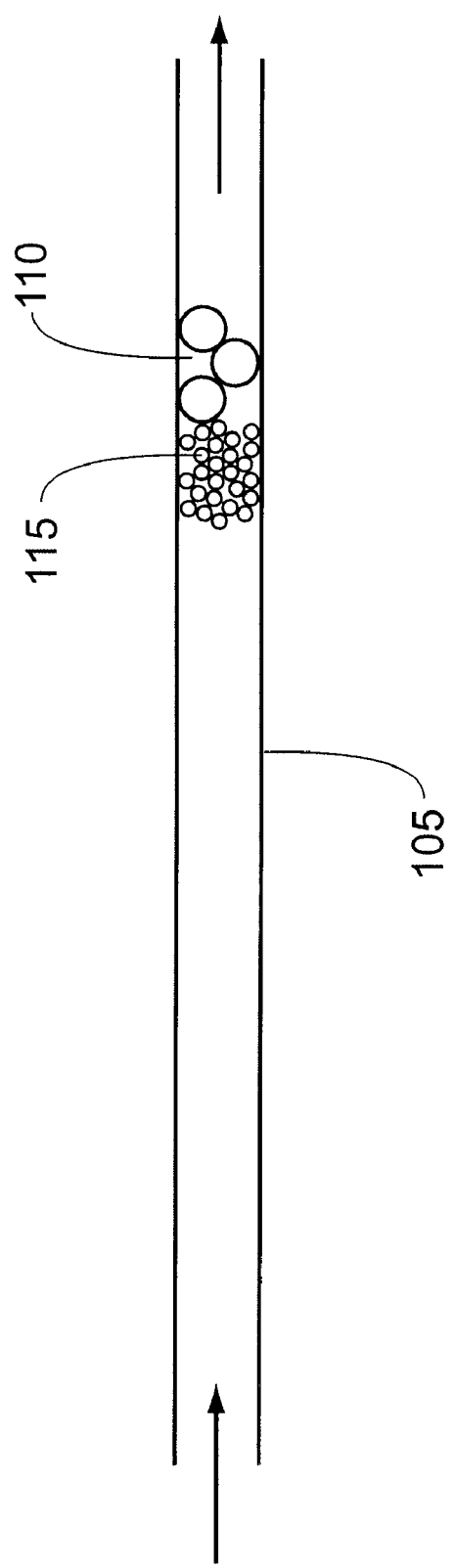

SEQUENCING BY INCORPORATION

CROSS-REFERENCE TO RELATED APPLICATIONS

The present application claims benefit of and priority to U.S. Ser. No. 60/121,223, entitled "Manipulation of Microparticles in Microfluidic Systems," filed Feb. 23, 1999 by Mehta et al.; U.S. Ser. No. 60/127,825 entitled "Manipulation of Microparticles in Microfluidic Systems," filed Apr. 5, 1999 by Mehta et al.; U.S. Ser. No. 60/128,643 entitled "Manipulation of Microparticles in Microfluidic Systems," filed Apr. 9, 1999 by Mehta et al.; co-filed U.S. application "Manipulation of Microparticles in Microfluidic Systems," filed Feb. 22, 2000, by Mehta et al.; co-filed PCT application entitled "Manipulation of Microparticles in Microfluidic Systems," filed Feb. 22, 2000, by Mehta et al.; and co-filed PCT application entitled "Sequencing by Incorporation" filed Feb. 22, 2000, Attorney Docket No. 01-006840PC by Parce et al.

STATEMENT REGARDING FEDERALLY SPONSORED RESEARCH OR DEVELOPMENT

The present invention was made with government funding from the United States National Institute of Standards and Technology (NIST), through the Advanced Technology Program (ATP) under Grant No. 70NANB8H4000, and the United States government may have certain rights in the invention.

BACKGROUND OF THE INVENTION

Most DNA sequencing today is carried out by chain termination methods of DNA sequencing. The most popular chain termination methods of DNA sequencing are variants of the dideoxynucleotide mediated chain termination method of Sanger. See, Sanger et al. (1977) Proc. Nat. Acad. Sci., USA 74:5463–5467. For a simple introduction to dideoxy sequencing, see, Current Protocols in Molecular Biology, F. M. Ausubel et al., eds., Current Protocols, a joint venture between Greene Publishing Associates, Inc. and John Wiley & Sons, Inc., (e.g., Supplement 38, current through 1998) (Ausubel), Chapter 7. Thousands of laboratories employ dideoxynucleotide chain termination techniques. Commercial kits containing the reagents most typically used for these methods of DNA sequencing are available and widely used. In addition to the Sanger methods of chain termination, new PCR exonuclease digestion methods have also been developed for DNA sequencing. Direct sequencing of PCR generated amplicons by selectively incorporating boronated nuclease resistant nucleotides into the amplicons during PCR and digestion of the amplicons with a nuclease to produce sized template fragments has been performed (Porter et al. (1997) Nucleic Acids Research 25(8):1611–1617). The above methods typically require that the terminated fragments be sequenced upon completion of the reaction. This is a time consuming step that limits the ability to sequence in a high throughput manner.

The development of microfluidic technologies by the inventors and their co-workers has provided a fundamental shift in how artificial biological and chemical processes are performed. In particular, the inventors and their co-workers have provided microfluidic systems that dramatically increase throughput for biological and chemical methods, as well as greatly reducing reagent costs for the methods. In these microfluidic systems, small volumes of fluid are moved through microchannels by electrokinetic or pressure-based mechanisms. Fluids can be mixed, and the results of the mixing experiments determined by monitoring a detectable signal from products of the mixing experiments.

Complete integrated systems with fluid handling, signal detection, sample storage and sample accessing are available. For example, Parce et al. "High Throughput Screening Assay Systems in Microscale Fluidic Devices" WO 98/00231 and Knapp et al. "Closed Loop Biochemical Analyzers" (WO 98/45481; PCT/US98/06723) provide pioneering technology for the integration of microfluidics and sample selection and manipulation. For example, in WO 98/45481, microfluidic apparatus, methods and integrated systems are provided for performing a large number of iterative, successive, or parallel fluid manipulations. For example, integrated sequencing systems, apparatus and methods are provided for sequencing nucleic acids. This ability to iteratively sequence a large nucleic acid (or a large number of nucleic acids) provides for increased rates of sequencing, as well as lower sequencing reagent costs. Applications to compound screening, enzyme kinetic determination, nucleic acid hybridization kinetics and many other processes are also described by Knapp et al.

New or improved methods of sequencing are accordingly desirable, particularly those that take advantage of high-throughput, low cost microfluidic systems. The present invention provides these and other features by providing new sequencing methods and high throughput microscale systems for providing sequencing reactions as well as many other features that will be apparent upon complete review of the following disclosure.

SUMMARY OF THE INVENTION

The present invention provides novel methods of sequencing by synthesis or incorporation. Nucleotides or nucleotide analogs are added to reaction mixtures comprising nucleic acid templates and primers, e.g., DNA or RNA. The nucleotides are incorporated into the primer, resulting in an extended primer. The sequence is determined as each additional complementary nucleotide is incorporated into the primer and the steps are repeated until the entire template sequence or a portion thereof is determined.

In one embodiment, the nucleotides or nucleotide analogs, or a fraction thereof, comprise a 3'-blocking group and a detectable label moiety, which typically comprises a phosphate or a carbamate group. The 3'-blocking groups provide reversible chain termination. When added to a growing nucleic acid chain, these nucleotide analogs result in a non-extendable primer. The 3'-blocking group is typically removed, e.g., by a reducing agent and/or a phosphatase, to produce an extendable primer to which further nucleotides are added, thereby allowing continued sequencing of the nucleic acid template. Removal of the 3'-blocking group is optionally performed before or after detection of the added nucleotide.

In another embodiment, the nucleotides or nucleotide analogs comprise a fluorescent label. Sequencing by synthesis using fluorescent nucleotides typically involves photobleaching the fluorescent label after detecting an added nucleotide. Photobleaching comprises applying a light pulse that destroys or reduces to an acceptable level, e.g., a background level or to a low enough level to prevent signal buildup over several sequencing cycles, the fluorescence of the nucleotides, e.g., a fluorescent nucleotide that has been added to the primer. The light pulse is typically applied for about 20 seconds or less, about 10 seconds or less, about 2 seconds or less, about 1 second or less, or about 0.1 second or less. The light pulse typically has a wavelength equal to the wavelength of light absorbed by the fluorescently labeled nucleotides. Detection of the added fluorescently labeled nucleotide occurs prior to or concurrent with photobleaching of the fluorescently labeled nucleotides and/or the extended primer. Nucleic acid templates comprising about 50 or more nucleotides, about 100 or more nucleotides, about 500 or more nucleotides, about 1000 or more nucleotides, about 2000 or more nucleotides, or about 10,000 or more nucleotides are optionally sequenced using these methods, e.g., sequenced with at least about 80%, at least about 90%, or at least about 95% accuracy.

In another embodiment, sequencing comprises sequencing by synthesis using detection of intercalating dyes ("sequencing by intercalation"). An intercalating dye is incubated or mixed with the template and primer as the sequencing reactions occur. When a nucleotide, e.g., a naturally occurring, non-labeled nucleotide, is incorporated into the primer, it forms an extended double-stranded region, into which intercalating dyes insert, e.g., between the stacked bases. The intercalating dye is detected, thus detecting the addition of a nucleotide to the growing chain and sequencing the template nucleic acid. The intercalating dye optionally comprises ethidium, ethidium bromide, an acridine dye, an intercalating nucleic acid stain, a cyanine dye, such as SYBR green, proflavin, propidium iodide, acriflavin, proflavin, actinomycin, anthracyclines, or nogalamycin. In some embodiments, photobleaching is performed after detecting the intercalating dye or approximately concurrent with detecting the intercalating dye.

The nucleotides or nucleotide analogs in the present invention typically comprise nucleoside 5'-triphosphates (dNTPs), e.g., deoxyadenosine 5'-triphosphate (dATP), deoxyguanosine 5'-triphosphate (dGTP), deoxycytidine 5'-triphosphate (dCTP), deoxythymidine 5'-triphosphate (dTTP), deoxyuridine 5'-triphosphate (dUTP), adenosine 5'-triphosphate (ATP), guanosine 5'-triphosphate (GTP), cytidine 5'-triphosphate (CTP), uridine 5'-triphosphate (UTP), or analogs thereof.

In some embodiments, the nucleotides or nucleotide analogs, or a fraction thereof, comprise a detectable label moiety, e.g., a fluorescent or chemiluminescent label moiety. Different nucleotides optionally comprise detectably different labels, e.g., ATP, GTP, CTP, TTP, and UTP each optionally comprising a distinguishable label.

The nucleotides are optionally incubated with the nucleic acids in series or in combination. For example, four detectably different nucleotides, e.g., reversible chain terminating nucleotide analogs, are optionally simultaneously incubated with template, primer, and polymerase. The added nucleotide stops chain growth, is detected, and then the chain terminating portion of the nucleotide is removed, e.g., the 3'-blocking group is removed to allow further extension of the primer. For example, the 3'-blocking group is optionally removed in a buffer or wash that also removes all unincorporated nucleotides. Alternatively, the 3'-blocking group comprises the label moiety and is detected after removal.

Alternatively, four nucleotides are added in series, one after the other. For example, one nucleotide is added, unincorporated nucleotides are removed from the reaction, and a fluorescent signal is detected, e.g., from a fluorescently labeled nucleotide added to the primer chain or from an intercalating dye that has intercalated into the recently extended double-stranded nucleic acid region. A second nucleotide is added, a third, and so on, e.g., until the nucleic acid template or a portion thereof is sequenced.

In another aspect, the methods involve performing the sequencing, e.g., by incorporation, by photobleaching, by intercalation, and the like, in a microfluidic device. Nucleic acid templates, e.g., DNA or RNA, and primers, are flowed through a microscale channel and contacted by a polymerase and one or more nucleotides or nucleotide analogs in the microscale channel, thereby adding at least one of the one or more nucleotides or nucleotide analogs to the primer. The added nucleotide or nucleotide analog is detected and the steps are repeated, e.g., to obtain an entire sequence or a portion thereof.

In one embodiment, the template and/or primer are attached to a set of particles, e.g., an ordered array of particles, which is flowed through a microscale channel or positioned, e.g., in a fixed location, within the microscale channel. The sequencing reagents, e.g., a train of reagents, are flowed across the particles to sequence the template nucleic acid. Unincorporated nucleotides or reagents are flowed through the microchannel, e.g., to a waste reservoir. Alternatively, the particle sets are flowed through the train of reagents to perform the sequencing. In some embodiments, the reagents are attached to particle sets and the template is flowed through the particle sets to be sequenced. When a nucleotide or nucleotide analog is added to the primer, a signal is typically detected from the added nucleotide, e.g., on the particle sets or released from the particle set and flowed through a detection region.

The particle sets optionally comprise about 1 or more particles, about 10 or more particles, about 100 or more particles, about 1000 or more particles, or about 10,000 or more particles. In some embodiments, the set of particles comprises a set of beads, which beads are selected from: polymer beads, silica beads, ceramic beads, clay beads, glass beads, magnetic beads, metallic beads, paramagnetic beads, inorganic beads, and organic beads; and wherein the beads have a shape, which shape is selected from one or more of: spherical, helical, cylindrical, spheroid, irregular, rod-shaped, cone-shaped, cubic, and polyhedral.

The train of reagents that is used to perform sequencing of a nucleic acid template typically comprises sequencing reagents for performing sequencing, e.g., sequencing by synthesis, e.g., with detection by photobleaching, by pyrosequencing chemistry, or by intercalation. Typical reagents include, but are not limited to, one or more of: a template, a primer, a polymerase, a sufurylase, an apyrase, an inorganic phosphate, ATP, a thermostable polymerase, luciferin, luciferase, an endonuclease, an exonuclease, $Mg^{++}$, a molecular crowding agent, a buffer, a dNTP, a salt, a phosphatase, a reducing agent, a modified dNTP, a nucleotide, a nucleotide analog, a nucleotide analog comprising a 3'-blocking group, a nucleotide analog comprising a 3'-phosphate group, a nucleotide analog comprising a 3'-carbamate group, a chain-terminating nucleotide analog, a reversible chain terminating nucleotide analog, a fluorescently labeled nucleotide, and an intercalating dye.

The particles and the reagent train are typically flowed through the microscale channel by one or more of: pressure, centripetal force, centrifugal force, a moving magnetic field, and an electrokinetic force.

Microfluidic devices for sequencing a nucleic acid are also provided. The devices typically comprise a body structure having a microscale cavity disposed therein; and a set of particles, e.g., an ordered array of particles as described above, disposed within the microscale cavity. The set of particles comprises at least one set of nucleic acid templates and at least one set of nucleic acid primers. Nucleotides and/or nucleotide analogs, as described above, are also disposed within the device, e.g., in reservoirs or attached to one or more particle sets.

BRIEF DESCRIPTION OF THE FIGURES

FIG. 1: Schematic illustration of a particle set in a microscale channel or capillary useful for sequencing, e.g., a nucleic acid template, by synthesis or incorporation.

DETAILED DISCUSSION OF THE INVENTION

Figure 2B:
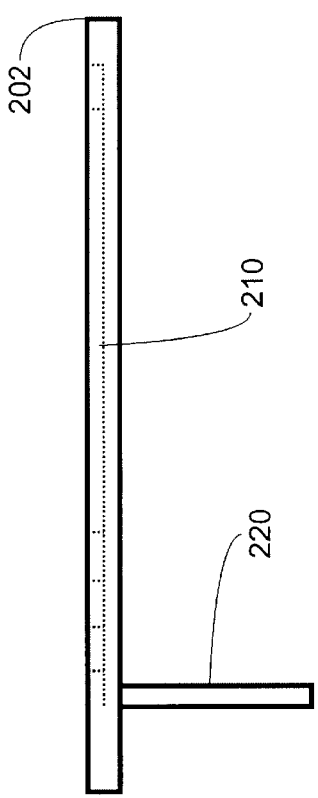
FIG. 2: Panels A, B, and C are schematic drawings of an integrated system of the invention, including a body structure, microfabricated elements, and a pipettor channel.

The present invention provides methods of sequencing nucleic acids by synthesis or incorporation.

Chemical structure definitions

As used herein formula (I) refers to a compound having the formula:

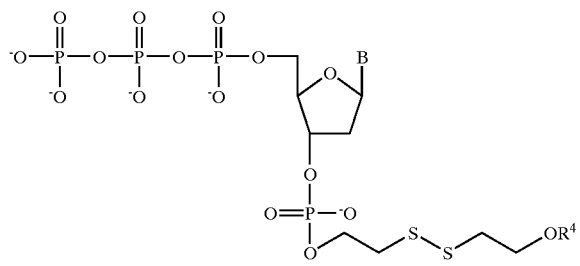

(I)

wherein $R^4$ comprises one or more of a linker moiety and a detectable label and B comprises one or more of a nitrogenous base and the detectable label. A detectable label typically comprises fluorescent or chemiluminescent moiety, e.g., to detect the nucleotide after it has been added to a growing primer strand. A "label" is any composition detectable by spectroscopic, photochemical, biochemical, immunochemical, electrical, optical or chemical means. Useful labels in the present invention include fluorescent dyes (e.g., fluorescein, Texas red, rhodamine, and the like), radiolabels (e.g., $^3H$, $^{125}I$, $^{35}S$, $^{14}C$, $^{32}P$, $^{33}P$, etc.), enzymes (e.g., horse-radish peroxidaase, alkaline phosphatase etc.), and colorimetric labels such as gold colored glass or plastic e.g., polystyrene, polypropylene, latex, etc.) beads. Preferred label moieties in the present invention include, but are not limited to, fluorescein and rhodamine.

The label is coupled directly or indirectly to a component of the assay according to methods well known in the art. As indicated above, a wide variety of labels are used, with the choice of label depending on the sensitivity required, ease of conjugation with the nucleotide, nucleoside, nitrogenous base, or the like, stability requirements, available instrumentation and disposal provisions. Non-radioactive labels are often attached by indirect means. Generally, a ligand molecule (e.g., biotin) is covalently bound to the component to be labeled. For example, a label is optionally covalently bound to the nitrogenous base moiety of a nucleotide or to the sugar moiety, e.g., at the 3'-position, through a linker bound to the 3'position of a nucleotide, or to a 3'-blocking group. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands are optionally used. Where a ligand has a natural anti-ligand, for example, biotin, thyroxine, or cortisol, it is used in conjunction with the labeled naturally occurring anti-ligand. Alternatively, any haptogenic or antigenic compound is used in combination with an antibody (see, e.g., Coligan (1991) *Current Protocols in Immunology,* Wiley/Greene, N.Y.; and Harlow and Lane (1989) *Antibodies: A Laboratory Manual,* Cold Spring Harbor Press, NY for a general discussion of how to make and use antibodies). The components of the invention are also optionally conjugated directly to signal-generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include, e.g., luciferin and 2,3,-dihydrophthalalzinediones, e.g., luminol.

A linker moiety or linker molecule in the present invention typically connects a 3'-blocking group to a detectable label. In some embodiments, the linker forms a portion of the 3'-blocking group. Linkers that are optionally used to provide a detectable label moiety are described above. Other chemical linkers include, but are not limited to, an acyl, an S-acyl, an alkyl, an aromatic, an acetyl, or an heteroaromatic group, or the like.

A nitrogenous base typically comprises a heterocyclic base such as adenine, guanine, thymine, cytosine, or any other purines, pyrimidines or derivative thereof.

Formula (II) refers to any compound having the formula:

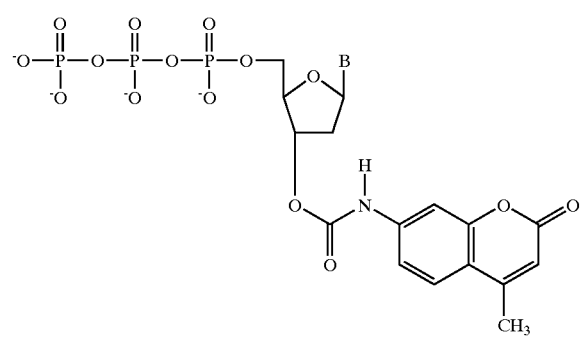

(II)

wherein B comprises one or more of a nitrogenous base and the detectable label, as described above. Alternatively, a label moiety is attached to the carbamate linker group.

Formula (III) refers to any compound having the formula:

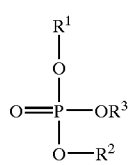
(III)

wherein $R^1$ comprises a nucleoside, a nucleotide, a nucleotide analog, a nucleoside analog, or the 3'-end of a growing nucleic acid chain, e.g., a primer, $R^2$ comprises a blocking moiety, which blocking moiety comprises a detectable label, and $R^3$ comprises a hydrogen or a negative charge. The blocking moiety comprises any chemical or biological moiety that prevents addition of another nucleotide or nucleotide analog to the growing nucleic acid, e.g., to $R^1$, and is removable, e.g., chemically or enzymatically. Removal of the blocking group typically results in a molecule having formula (VII) or formula (VIII) as described below.

Formula (IV) refers to any compound having the formula:

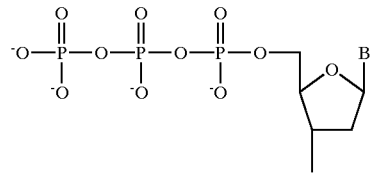
(IV)

wherein B comprises a nitrogenous base, as described above.

Formula (V) refers to any compound having the formula:

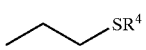
(V)

wherein $R^4$ comprises one or more of: a linker moiety and a detectable label. Formula (V) optionally serves as the blocking moiety for formula (III).

Formula (VI) refers to any compound having the formula:

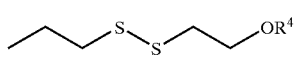
(VI)

wherein $R^4$ comprises one or more of: a linker moiety and a detectable label. Formula (VI) also provides an example blocking group as used in formula (III).

Formula (VII) refers to any compound having the formula:

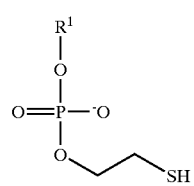
(VII)

wherein $R^1$ comprises a nucleotide, nucleotide analog, nucleoside, nucleoside analog, a nucleic acid, a primer, or the like.

Formula (VIII) refers to any compound having the formula:

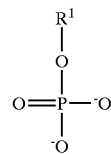
(VIII)

wherein $R^1$ comprises a nucleotide, nucleoside, nucleotide analog or nucleoside analog, a hucleic acid, a primer, or the like.

Formula (IX) refers to any compound having the formula:

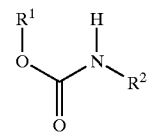
(IX)

wherein $R^1$ comprises a nucleoside, a nucleotide, a nucleoside analog, a nucleotide analog, a nucleic acid, a primer, or the like and $R^2$ comprises a linker moiety, and either $R^1$ or $R^2$ further comprises a detectable label. For example, a detectable label is optionally attached to the nitrogenous base of $R^1$.

Formula (X) refers to any compound having the formula:

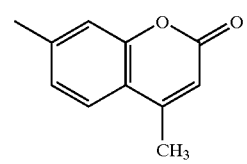
(X)

Formula (X) provides an example linker molecule ($R^2$) for formula (IX).

I. Introduction

The present invention provides novel methods for sequencing nucleic acids, e.g., in microfluidic devices, e.g., using particle arrays. The sequencing methods provided comprise sequencing by incorporation or synthesis. Sequencing by incorporation refers to a method of determining the sequence or order of nucleotides in a nucleic acid, e.g., DNA or RNA, e.g., without chain degradation or termination and subsequent separation. A nucleotide or nucleotide analog is added to a primer strand, e.g., complementary to the template strand, and detected as added. Additional nucleotides are then added to the same primer strands, i.e., the strands are not permanently terminated. In some embodiments, the growing primer strand is reversibly terminated, i.e., it is temporarily terminated and then termination is reversed, e.g., by removal of a blocking group. In other embodiments, a fraction of the chains are terminated while another fraction is synthesized to the end, with detection after each nucleotide addition.

The present invention provides at least four new methods of sequencing by synthesis: (1) sequencing using a 3'-phosphate blocking group; (2) sequencing using a 3'-carbamate blocking group; (3) sequencing by synthesis with detection by photobleaching ("sequencing by photobleaching"); and (4) sequencing by synthesis using detection of intercalating dyes ("sequencing by intercalation").

Sequencing using blocking groups, e.g., phosphate and carbamate nucleotide analogs, typically involves reversibly terminating growing nucleic acid strands. For example, the presence of the blocking group prevents additional nucleotides from being incorporated into the primer strand, but the blocking group is removable or cleavable allowing synthesis of the primer strand to continue when desired, e.g., after detection.

Sequencing by photobleaching typically involves the uses of fluorescently labeled nucleotides to synthesize a primer nucleic acid that is complementary to the template nucleic acid. Photobleaching reduces the intensity of the signal, which builds with each addition of a fluorescently labeled nucleotide to the primer strand. By reducing the signal intensity, longer DNA templates are optionally sequenced.

Sequencing by intercalation relies on an intercalating dye to provide detection of an added nucleotide. Nucleotides are added one at a time to a growing strand and detected due to a signal from an intercalating dye that is differentially associated with the extended nucleic acid strand. The dye inserts between the stacked bases of a double helical nucleic acid. As the primer strand grows, the double-stranded region continually increases in length, e.g., until it is as long as the template or a desired length. The more bases that are added to the primer, the more intercalation occurs, thus providing a signal increase from which the addition of a nucleotide is detected. In some embodiments, the intercalating dyes are photobleached after incorporation to reduce signal intensity.

The above methods all represent types of sequencing by synthesis because at least a portion of the growing primer strands are synthesized, e.g., to the end, as opposed to being terminated, e.g., mid-length. The methods are optionally practiced in microfluidic devices, e.g., using particle arrays, in capillaries, in microwell plates, or the like.

II. General description of sequencing by incorporation

The present invention provides a plurality of methods for sequencing by synthesis or incorporation. In particular, reversible chain termination methods are provided. For example, primer strands are terminated by the addition of a nucleotide comprising a blocking group and then the blocking group is removed to allow further elongation. In a second embodiment, sequencing by synthesis is performed using fluorescently labeled nucleotides and periodically photobleaching the growing primer strand to reduce fluorescent signal build up. Alternatively, the signal is allowed to build up and detected without photobleaching. In a third embodiment, unlabeled nucleotides are added to growing primer strands and detected by detecting an increase in intercalation. Intercalation increases as the length of the double strand nucleic acid increases. Therefore the signal level increases as each additional complementary nucleotide is added to the growing primer/template strand.

A number of basic sequencing by incorporation methods are known, e.g., as set forth in Hyman U.S. Pat. Nos. 4,971,903; Malemede 4,863,849; Cheeseman 5,302,509, and Canard 5,798,210. Generally, any detectable event associated with incorporation of a nucleotide can be used to monitor sequencing reactions. In sequencing by incorporation methods, incorporation of nucleotides or nucleotide analogs into nucleic acids, e.g., using a polymerase to extend a primer hybridized to a complementary template nucleic acid, is monitored to provide an indication of the sequence of the template nucleic acid. This can be performed by selectively adding reagents comprising labels such as bases comprising fluorescent moieties, e.g., four detectably different fluorescent moieties, to e.g., a member of an array set comprising the template nucleic acid and monitoring incorporation of the label into the nucleic acid. The present invention provides new or improved methods of sequencing by incorporation, e.g., by using alternative detectable events, such as the addition of an intercalator to a double-helix; the addition of a labeled nucleotide to a primer, by providing reversible chain terminating nucleotides; or by photobleaching to insure detectable addition of nucleotides at any desired read length.

Generally, sequencing by incorporation involves providing a nucleic acid template and a primer, which are hybridized to form a double-stranded nucleic acid region, which is sequentially extended by addition of complementary nucleotides to the primer strand. "Nucleic acid template" refers to a polynucleotide chain utilized, e.g., during DNA replication or transcription, as a guide to the synthesis of a second polynucleotide chain with a complementary base sequence. The template nucleic acids of the present invention typically comprise DNA or RNA and typically comprises about 50 or more, about 500 or more, about 1000 or more, about 2000 or more nucleotides, or about 10,000 or more nucleotides.

The template is typically hybridized or annealed to a primer, forming a double stranded nucleic acid region that is extended by adding bases to the primer strand. The primer comprises a short stretch of nucleotides, e.g., DNA or RNA, that is elongated by a polymerase, e.g., a DNA polymerase, taq polymerase, other thermostable polymerases, room temperature polymerases, and the like. The elongated or extended primer is synthesized in the presence of polymerase and one or more nucleotides or nucleotide analogs to produce a nucleic acid that is complementary to the template strand. Each addition of a nucleotide or nucleotide analog extends the double-stranded region of the nucleic acid.

The nucleic acid and primer are typically hybridized and incubated or mixed with one or more nucleotides or nucleotide analogs in the presence of a polymerase. The nucleotides are added to the primer strand to produce an extended primer. The extended primer is a nucleic acid primer that has had one or more nucleotides added to it, e.g., nucleotides that are complementary to the annealed template. Each added nucleotide is detected to determine the sequence of the template. The term, "nucleotides" is used herein to refer to the building blocks of nucleic acids, including, but not limited to, naturally occurring and non-naturally occurring nucleotides, nucleosides, nucleotide analogs, nucleoside analogs, and the like. Nucleosides typically comprise a nitrogenous base and a sugar, e.g., deoxyribose, ribose, or the like. Nucleotides generally comprise a nitrogenous base, a sugar, and a phosphate group, e.g., a monophosphate, a diphosphate, or a triphosphate. "Nitrogenous base" refers to heterocyclic bases such as adenine, guanine, thymine, cytosine, other purines and pyrimidines and derivatives thereof. Nucleotides used in the present invention typically comprise 5'-nucleoside phosphates including, but not limited to, deoxyadenosine 5'-triphosphate, deoxyguanosine 5'-triphosphate, deoxycytidine 5'-triphosphate, deoxythymidine 5'-triphosphate, deoxyuridine 5'-triphosphate, adenosine 5'-triphosphate, guanosine 5'-triphosphate, cytidine 5'-triphosphate, uridine 5'-triphosphate, thymidine-5'-triphosphate, and analogs thereof.

"Nucleotide analog" is used herein to refer to compounds, e.g., derivatives of nucleosides and nucleotides, that are optionally incorporated into a growing nucleic acid chain, e.g., added to a primer or extended primer to form an extended double stranded region. Preferred nucleotide analogs include, but are not limited to, compounds comprising a 3'-blocking group, e.g., a chain terminating blocking group or a reversible chain terminating blocking group. Blocking groups of the present invention typically comprises a phosphate or a carbamate group. Preferred nucleotide analogs include, but are not limited to, compounds comprising one or more of the structures represented by formulas (I), (II), (III), (IV), (V), (VI), (VII), (VIII), (IX), and (X), as described above.

Other nucleotide analogs of the present invention include nucleotides comprising a label moiety, e.g., a detectable label moiety. Detectable label moieties include, but are not limited to, fluorescent moieties and chemiluminescent moieties. Nucleotide and nucleoside analogs of the present invention are optionally synthetic, naturally occurring, or non-naturally occurring compounds that have similar properties to nucleotides and nucleosides and are typically metabolized in a similar manner. Other examples include, but are not limited to, phosphorothioates, phosphoroamidates, methyl phosphonates, chiral-methylphosphonates, 2-O-methyl ribonucleotides, dideoxynucleotides, boronated nucleotides, and the like.

When chain terminating nucleotide analogs are used to extend a primer in a sequencing reaction, the extended primer becomes a non-extendable primer upon addition of the chain terminating nucleotide analog. A "non-extendable primer" is a primer or nucleic acid fragment to which the relevant polymerase, i.e., the polymerase in the reaction mixture, will not add another nucleotide or nucleotide analog, i.e., because the 3'-OH group is blocked, e.g., by a carbamate or phosphate group. The chain terminates and no more nucleotides are added.

In the present invention, a preferred nucleotide analog is a reversible chain terminating nucleotide. These nucleotides, when added to a growing primer chain, terminate the chain by the addition of the nucleotide analog, e.g., the blocking group, and thereby inhibit the addition of any other nucleotides. The terminated primer is then subjected to a reaction that reverses the termination. For example, adding a nucleotide comprising a 3'-blocking group to a growing nucleic acid chain terminates the chain and inhibits further additions of nucleotides. However, the chain terminating 3'-blocking group is optionally removed to allow addition or growth of the chain to continue. For example, reagents that destroy the blocking group are optionally added to the reaction mixtures. Preferred reversible chain terminating nucleotides and blocking groups are described in more detail below. Non-terminating nucleotides and nucleotide analogs are those that allow further addition of nucleotides to a growing chain of nucleotides. For example, a non-terminating nucleotide typically contains a 3'-OH group so that another nucleotide is optionally added to the 3'-terminus of the growing nucleic acid chain. The chain terminating nucleotides typically contain a blocking group on the 3'OH. A "blocking group" typically prevents addition of a nucleotide to the 3'-terminus of a nucleic acid. Blocking groups are typically chemical moieties that are attached to the nucleic acid or nucleotide in the 3'-position to prevent further binding or reactions at that position. Preferred blocking groups of the present invention include, but are not limited to, phosphate and carbamate groups, e.g., 3'-phosphates and 3'-carbamates. For more information on blocking groups, see, e.g., *Protective Groups in Organic Synthesis,* by T. Greene, Wiley and Sons, New York (1981).

After adding a nucleotide, e.g., to a growing primer chain, unincorporated nucleotides are optionally removed from the reaction, e.g., by washing a channel or capillary, e.g., with a buffer. Added nucleotides are then detected, e.g., by detecting a fluorescent or chemiluminescent signal from the added nucleotide. "Unincorporated nucleotides" are those nucleotides that were not incorporated or added into the nucleic acid chain. In some embodiments, the unincorporated nucleotides are left in the reaction but rendered unincorporable, e.g., by chemical reaction or change in reaction conditions.

The present invention provides a plurality of methods for sequencing by synthesis, e.g., sequencing using 3'-blocking groups such as phosphate groups and carbamates groups, sequencing by photobleaching, sequencing using a low concentration of chain terminating labeled nucleotides in combination with non-terminating, non-labeled nucleotides, sequencing by synthesis using detection by intercalation, and the like. These methods are each discussed in more detail below In a preferred method, the sequencing reactions of the present invention are performed using immobilized templates and primers. For example, the templates and primers are optionally immobilized on a membrane or porous matrix or on the walls of a capillary, microfluidic channel or microwell. Alternatively, the template and primer are immobilized on a set of particles, which particles are then optionally flowed through a capillary or channels/chambers of a microfluidic device.

For example, the template and the primer are optionally attached to a particle array. The particle array is flowed through or positioned within, e.g., a capillary or microfluidic device. Sequencing reagents are optionally flowed across the particle array to sequence the template or the particle array is flowed through a train of reagents. Particle arrays are discussed in more detail in U.S. Ser. No. 60/128,643, filed Apr. 9, 1999 and in co-filed application, "Manipulation of Microparticles in Microfluidic Systems," by Mehta et al., which is hereby incorporated by reference.

When performed in a microfluidic device, the methods presented herein typically comprise flowing a nucleic acid template and a primer through a microscale channel, in which they are typically immobilized, hybridized and sequenced. Alternatively, a microfluidic device comprising a template and primer disposed therein is provided. Sequencing reagents, e.g., polymerase solutions, nucleotides, buffers and the like, are optionally flowed across the template and primer or the template and primer are flowed through the reagents. When the nucleotides and polymerase are incubated with the template and the primer, e.g., by flowing the nucleotides and polymerase across the template and primer, one or more nucleotides, e.g., complementary nucleotides, are optionally incorporated into the primer, producing an extended primer. The channel is optionally washed to remove any unincorporated nucleotides and then the added nucleotide is detected. The steps are then repeated to provide, e.g., the entire sequence of the template nucleic acid or a portion thereof.

In addition to providing novel sequencing methods, the present invention provides microfluidic sequencing methods. Sequencing by incorporation using any method described herein is optionally performed in a microfluidic device. In addition conventional sequencing methods are optionally improved by the use of microfluidic devices.

It is expected that one of skill is familiar with fundamental sequencing methodologies applicable to the present invention. Examples of techniques for making and sequencing nucleic acids by conventional methods, and instructions sufficient to direct persons of skill through most standard cloning and other template preparation exercises are found in Berger and Kimmel, Guide to Molecular Cloning Techniques, Methods in Enzymology volume 152 Academic Press, Inc., San Diego, Calif. (Berger); Sambrook et al.

(1989) Molecular Cloning—A Laboratory Manual (2nd ed.) Vol. 1–3, Cold Spring Harbor Laboratory, Cold Spring Harbor Press, NY, (Sambrook); and Current Protocols in Molecular Biology, F. M. Ausubel et al., eds., Current Protocols, a joint venture between Greene Publishing Associates, Inc. and John Wiley & Sons, Inc., (1997, supplement 37) (Ausubel). Basic procedures for cloning and other aspects of molecular biology and underlying theoretical considerations are also found in Lewin (1995) Genes V Oxford University Press Inc., NY (Lewin); and Watson et al. (1992) Recombinant DNA Second Edition Scientific American Books, NY. Product information from manufacturers of biological reagents and experimental equipment also provide information useful in known biological methods. Such manufacturers include the Sigma Chemical Company (Saint Louis, Mo.); New England Biolabs (Beverly, Mass.); R&D systems (Minneapolis, Minn.); Pharmacia LKB Biotechnology (Piscataway, N.J.); CLONTECH Laboratories, Inc. (Palo Alto, Calif.); ChemGenes Corp., (Waltham Mass.) Aldrich Chemical Company (Milwaukee, Wis.); Glen Research, Inc. (Sterling, Va.); GIBCO BRL Life Technologies, Inc. (Gaithersberg, Md.); Fluka Chemica-Biochemika Analytika (Fluka Chemie AG, Buchs, Switzerland); Invitrogen (San Diego, Calif.); Perkin Elmer (Foster City, Calif.); and Strategene; as well as many other commercial sources known to one of skill.

In one aspect, the generation of large nucleic acids is useful in practicing the invention, e.g., as templates fixed to array members, e.g., for sequencing long regions of nucleic acids, or for monitoring expression products by hybridization of biological materials to the fixed templates. It will be appreciated that such templates are particularly useful in some aspects where the methods and devices of the invention are used to sequence large regions of DNA, e.g., for genomics types of applications. An introduction to large clones such as YACs, BACs, PACs and MACs as artificial chromosomes is provided by Monaco and Larin (1994) Trends Biotechnol 12 (7): 280–286.

The construction of nucleic acid libraries of template nucleic acids is described in the above references. YACs and YAC libraries are further described in Burke et al. (1987) Science 236:806–812. Gridded libraries of YACs are described in Anand et al. (1989) Nucleic Acids Res. 17, 3425–3433, and Anand et al. (1990) Nucleic Acids Res. Riley (1990) 18:1951–1956 Nucleic Acids Res. 18(10): 2887–2890 and the references therein describe cloning of YACs and the use of vectorettes in conjunction with YACs. See also, Ausubel, chapter 13. Cosmid cloning is also well known. See, e.g., Ausubel, chapter 1.10.11 (supplement 13) and the references therein. See also, Ish-Horowitz and Burke (1981) Nucleic Acids Res. 9:2989–2998; Murray (1983) Phage Lambda and Molecular Cloning in Lambda II (Hendrix et al., eds) 395–432 Cold Spring Harbor Laboratory, NY; Frischauf et al. (1983) J.Mol. Biol. 170:827–842; and, Dunn and Blattner (1987) Nucleic Acids Res. 15:2677–2698, and the references cited therein. Construction of BAC and P1 libraries is well known; see, e.g., Ashworth et al. (1995) Anal Biochem 224 (2): 564–571; Wang et al. (1994) Genomics 24(3): 527–534; Kim et al. (1994) Genomics 22(2): 336–9; Rouquier et al. (1994) Anal Biochem 217(2): 205–9; Shizuya et al. (1992) Proc Natl Acad Sci U S A 89(18): 8794–7; Kim et al. (1994) Genomics 22 (2): 336–9; Woo et al. (1994) Nucleic Acids Res 22(23): 4922–31; Wang et al. (1995) Plant (3): 525–33; Cai (1995) Genomics 29 (2): 413–25; Schmitt et al. (1996) Genomics 1996 33(1): 9–20; Kim et al. (1996) Genomics 34(2): 213–8; Kim et al. (1996) Proc Natl Acad Sci U S A (13): 6297–301; Pusch et al. (1996) Gene 183(1–2): 29–33; and, Wang et al. (1996) Genome Res 6(7): 612–9.

In general, where the desired goal of a sequencing project is the sequencing of a genome or expression profile of an organism, a library of the organism's cDNA or genomic DNA is made according to standard procedures described, e.g., in the references above. Individual clones are isolated and sequenced, and overlapping sequence information is ordered to provide the sequence of the organism. See also, Tomb et al. (1997) Nature 539–547 describing the whole genome random sequencing and assembly of the complete genomic sequence of Helicobacter pylori; Fleischmann et al. (1995) Science 269:496–512 describing whole genome random sequencing and assembly of the complete Haemophilus influenzae genome; Fraser et al. (1995) Science 270:397–403 describing whole genome random sequencing and assembly of the complete Mycoplasma genitalium genome and Bult et al. (1996) Science 273:1058–1073 describing whole genome random sequencing and assembly of the complete Methanococcus jannaschii genome.

III. Sequencing a nucleic acid using reversible chain terminating nucleotide analogs comprising a 3'-blocking group In one embodiment, the present invention provides methods of sequencing by synthesis using nucleotide analogs with reversible chain terminating 3'-blocking groups. The blocking groups are used to temporarily stop nucleic acid synthesis after the addition of a nucleotide. While synthesis is temporarily blocked or terminated, the newly incorporated nucleotide is detected. The blocking groups are then removed and chain elongation continues, e.g., until the entire template is sequenced.

A template and a primer are provided and hybridized, i.e., and typically immobilized. For example, template and primer nucleic acids are optionally flowed through a microfluidic device or immobilized in a microwell plate. The template and primer are incubated with a polymerase and one or more nucleotide analogs comprising reversible chain terminating blocking groups. Complementary nucleotides are added to the primer strand, resulting in an extended primer, and detected, thereby providing an indication of the template strand sequence based on the identity of the nucleotide analog added to the primer. For example relevant nucleotides, e.g., C, A, G, T, and U, are optionally simultaneously incubated with the template and primer or each relevant nucleotide is added separately. When added together, each type of nucleotide comprises a detectably different label and detection identifies which nucleotide was added. When each of the nucleotides is added individually, e.g., in series, the nucleotides optionally comprise the same are different labels. In this case, detection determines if a nucleotide was added and if not, then the next nucleotide in the series is added. The steps are repeated until the entire template or a portion thereof is sequenced.

With chain terminating nucleotides analogs, the addition of the nucleotide inhibits further elongation of the primer. In previously known methods, some nucleic acids chains are terminated and sequencing continues with others and then all resulting fragments are separated after the sequencing reactions are complete and detected. In the present methods no separation is necessary, because the chain termination is reversible. The chain terminating group is removed from the growing nucleic acid chain after it is detected (or the group is optionally removed and then detected). The removal leaves an extendable primer to which another nucleotide is added.

The chain terminating nucleotides used in the present invention typically comprise a phosphate group or a carbamate group, e.g., as in formula (I), (II), (III) or (IX).

Phosphate Blocking Groups

In one embodiment, the blocking group of the present invention comprises a phosphate moiety. When added to a growing nucleic acid chain, e.g., a primer, the blocking group blocks nucleic aid growth until it is removed. The blocking group typically comprises a phosphate moiety and a linker moiety. The linker moiety, which optionally comprises a detectable label, is typically removed by chemical cleavage and the phosphate is typically removed by enzymatic cleavage.

The phosphate blocking group of the invention is typically bound to the 3'-OH position of a nucleotide, nucleotide analog, or nucleic acid. The phosphate blocking groups of the present invention typically comprise one or more phosphate moieties, and a blocking moiety. The blocking moiety typically comprises one or more of: a linker moiety, a disulfide moiety, a compound having formula (V), a compound having formula (VI), and a detectable label. Linkers and labels are described above. Typically a linker moiety is any molecule or portion thereof used to attach a label to a nucleotide analog, e.g., in this case to attach the label moiety to a blocking moiety, such as that of formula (V) or (VI). Typical linker groups comprise alkyl, acyl, acetyl and aromatic molecules. The most basic structure for a phosphate nucleotide analog of the invention is provided by Formula (III).

Nucleotides of interest are typically labeled, e.g., by attaching a detectable label to the 3'-blocking group. If all four nucleotides are labeled with a different label, they are optionally incubated with the template and primer in one batch and detection identifies which nucleotide was added. If the same label is used for all nucleotides of interest, the nucleotides are incubated with the template primer in series, detecting after each nucleotide, e.g., A, C, G, U, and T, in the series.

Examples of nucleotide analogs having phosphate blocking groups include, but are not limited to compounds having formula (I), (III), (VII), (VIII), and the like. The phosphate groups are typically removed after they are detected, e.g., a nucleotide analog is added to the growing chain, detected, and removed. Typically, detection comprises detecting a fluorescent moiety on the added nucleotide, e.g., to determine the nature or identity of the added nucleotide. A variety of fluorescent labels and methods of attachment to nucleotides are well known to those of skill in the art. Similar phosphate groups have been generated for use with protein derivatives. See, e.g., C. Mathe et al. J. Org. Chem. 63, 8547–8550 (1998); Gay et al., J. Chem. Soc. 8, 1123 (1970); and, Eckstein at al. Trendes in Biochem 14, 97 (1989).

Removal of the phosphate blocking group comprises removal of the linker and/or label moiety, removal of the blocking group moiety, and removal of the phosphate moiety. Removal of each section of the blocking group is optionally a separate step or one step, e.g., removal of the blocking moiety, the phosphate moiety and the linker moiety all occur simultaneously. For example, the linker and label moiety, e.g., a fluorescent dye are typically removed using a reducing agent, e.g., diborane, TCEP, disulfide reductase, dithiothreitol (DTT), glutathione, or the like. For further information reductions, e.g., of disulfides, see, e.g., March, *Advanced Organic Chemistry,* Fourth Edition, Wiley & Sons, New York, (1992). Removal of the linker and/or label typically results in a compound of formula (VII), which self cleaves, e.g., through an intramolecular nucleophilic attack, e.g., simultaneously with or right after the reduction, to produce a free 3'-phosphate group as shown in Formula (VIII). Any combination of linker moieties and blocking groups that result in a compound of formula (VII) or (VIII) are optionally used. For example, any arrangement of linkers, blocking groups, dyes, and the like, which when reduced or otherwise cleaved produces a compound of formula (VII), is optionally used to provide a nucleotide analog of the present invention. Compound (VII) comprises an unstable compound. Having a thiol group at a specific distance, e.g., the distance required for 2 $CH_2$ groups, from the phosphate moiety allows the compound to spontaneously degrade, e.g., through an intramolecular nucleophilic attack, e.g., sulfur acts as a nucleophile and causes the elimination of the blocking group from the phosphate group, to the compound of formula (VIII).

The phosphate group is optionally removed with a phosphatase, e.g., an alkaline phosphatase, a 3'-phosphatase, or any naturally occurring or non-naturally occurring enzyme comprising 3'-phosphatase activity, e.g., a kinase, e.g., T4 kinase, with 3'-alkaline phosphatase activity. The phosphatase removes the phosphate group from the nucleotide or nucleotide analog of formula (VIII), resulting in a free 3'-OH which is optionally extended by the addition of another nucleotide. Preferably, the phosphatase or other enzyme with phosphatase activity does not degrade the phosphodiester bonds of the DNA backbone. Alternatively, the 3'-phosphate is chemically cleaved.

Figure 4:
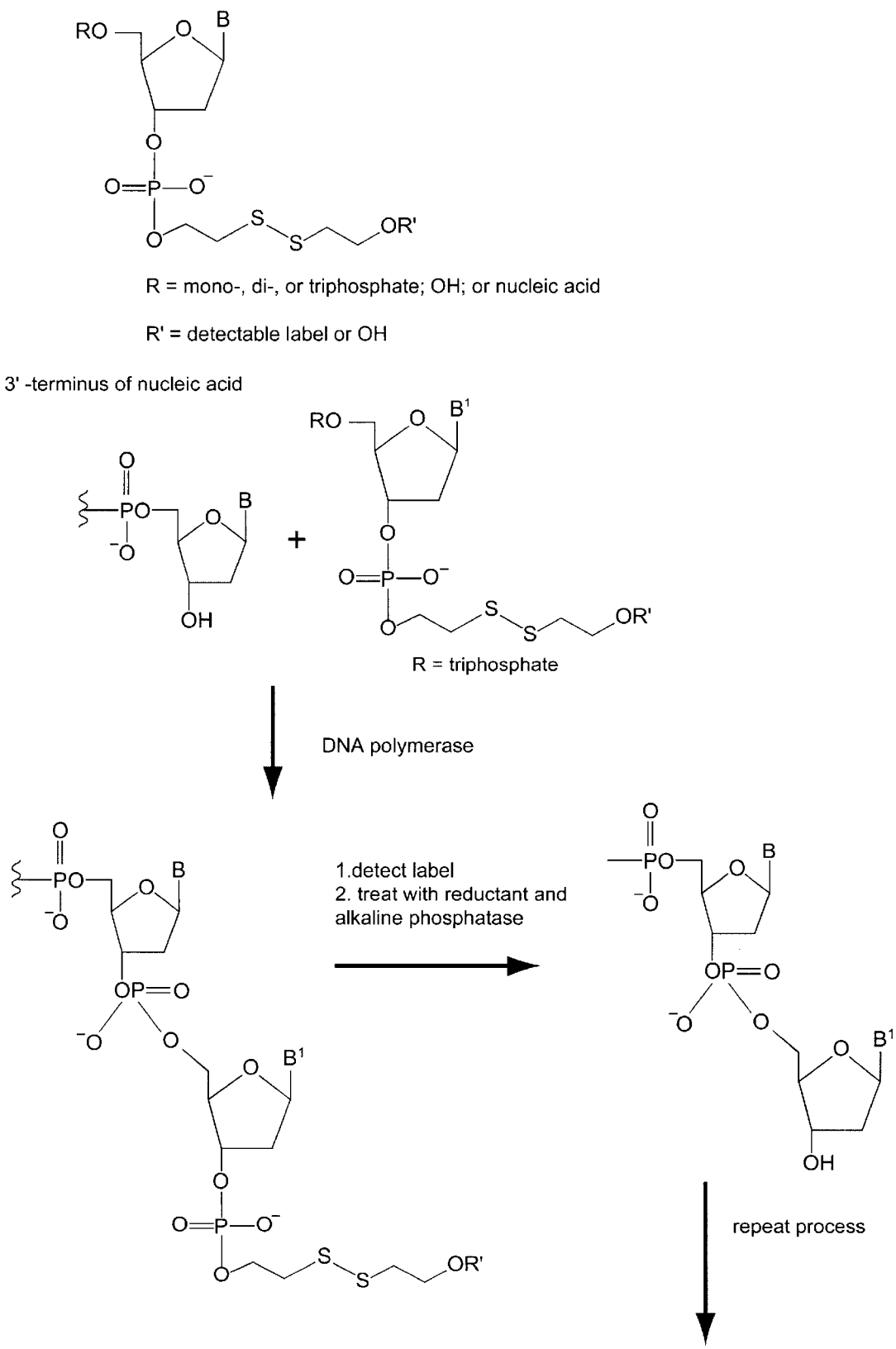
FIG. 4: A DNA sequencing scheme using phosphate/disulfide blocking groups.

For example, DTT and alkaline phosphatase are added to a sequencing reaction mixture, e.g., after detection of the most recently added nucleotide, to remove the blocking moiety, phosphate, linker and label moieties simultaneously. FIG. 4 provides a sequencing scheme using a phosphate blocking group that is removed as described above. One or more nucleotide analogs, e.g., with the bases: A, C, G, U, and T, are provided (FIG. 4, Panel A) wherein each nucleotide comprise a 3'-blocking group. The 3'-blocking group comprises a 3-'phosphate and a disulfide blocking group. In addition, the blocking group comprises any appropriate linker that is used to attach a detectable label moiety to the disulfide group. For example, A, C, G, and T are each given a different detectable label, e.g., four different fluorescent dyes. Methods of attaching labels, e.g., fluorescent dyes, to nucleotides and nucleotides analogs are well known to those of skill in the art. FIG. 4, Panel B illustrates the addition, e.g., in the presence of DNA polymerase, of the nucleotide from Panel A to the 3'-end of a growing DNA chain, e.g., a primer that is hybridized to the nucleic acid template being sequenced. The nature of the nucleotide added, e.g., A, C, G, or T, is determined by the template which is being sequenced. A complementary nucleotide is added. The DNA chain is thereby extended by one nucleotide, e.g., a nucleotide that is complementary to the template nucleic acid. However, the 3'-end comprises a blocking group that prevents further extension because the 3'OH is not free.

Unincorporated nucleotides are then optionally removed from the reaction mixture. For example, the template and primer are optionally attached to a membrane and the unincorporated nucleotides are washed from the membrane. The added nucleotide is then optionally detected, its identity determined by the fluorescent signal detected. Alternatively, the template is incubated with one base at a time, e.g., A, C, G, or U, is mixed in series with template until the complementary one is added and detected.

The blocking group is then removed as shown in Panel C. The extended DNA chain is treated, e.g., with DTT, and alkaline phosphatase, resulting in a DNA chain with an extendable 3'OH. If not detected after removal of unincorporated nucleotides, the blocking group comprising the label is optionally detected after the removal of the blocking group from the extended DNA chain. The removed blocking groups provide a signal, e.g., a fluorescent signal that is optionally detected, e.g., before discarding the removed blocking groups. The process is then repeated to determine additional nucleotides in the sequence of the DNA template.

For further information on types of reducing agents and linkers that are optionally cleaved, e.g., to produce a compound of formula (VII) or (VIII), see, e.g., March, *Advanced Organic Chemistry,* Fourth Edition, Wiley & Sons, New York, (1992); and Carey and Sundberg, *Advanced Organic Chemistry,* Parts I and II, Third Edition, Plenum Press, New York, (1990).

Carbamate Blocking Groups

In other embodiments, nucleic acid synthesis is temporarily terminated by a nucleotide comprising a removable carbamate blocking group. The blocking group comprises a carbamate linkage, e.g., between a linker and/or label moiety and the 3'-position of a nucleic acid or nucleotide. The carbamate group is typically attached to the nucleotide or nucleotide analog such that it blocks the 3'-OH and thus blocks incorporation of additional nucleotides or nucleotide analogs, e.g., to the growing primer strand. The carbamate group is optionally cleaved to allow further strand elongation and further sequencing.

A carbamate group is optionally added to a 3'-OH of a nucleotide or nucleic acid, e.g., through reactions with various amines. The carbamate linkage is subject to attack, e.g., with an esterase, a mild base, or a hydroxyl amine, to produce a free 3'OH group. Therefore, the carbamate nucleotide analogs are optionally used as the analogs described above. The nucleotides are incubated with the template and primer and when a nucleotide is added to the primer, it terminates the chain. However, the carbamate linkage is then optionally cleaved to provide an extendable primer.

Example carbamate nucleotides include, but are not limited to, those of formula (II) and (IX). The carbamate nucleotides are typically labeled and detected as described above. In some embodiments, the carbamate, which includes a detectable label is cleaved from the extended primer and then detected.

In one embodiment, the carbamate nucleotides analogs are used to sequence a nucleic acid in a capillary comprising, e.g., a particle retention element or particle capture region. For example FIG. 1 provides capillary 105 and particle retention element 110. As shown particle retention element comprises a set of particles, e.g., epoxy coated particles, which are immobilized in capillary 105. Particle set 110 forms a particle capture region by forming a porous barrier. In other embodiments, the porous barrier or particle retention element is optionally a frit or a constriction in the channel, e.g., a narrow channel region. Templates and/or primers are optionally attached to particle set 115, e.g., through biotin-avidin binding or biotin-streptavidin binding, either before or after the particle set has been fixed in capillary 105. Particle set 115 is captured or retained by particle set 110 because the mean diameter of the particles in particle set 115 is larger than the pore size created by particle set 110. Alternatively, particle set 115 is held in place by magnetic force or by chemically binding to the channel or capillary. A train of reagents is then flowed across particle set 115 to sequence the template. For example a set of nucleotide analogs comprising carbamate blocking groups is flowed across the template, thus adding a complementary base to the primer. For example, nucleotide analogs comprising, e.g., ATP, GTP, CTP, and TTP with carbamate blocking groups and detectably different labels are optionally flowed across particle set 115. Unincorporated nucleotides are removed from capillary 105, e.g., by washing a buffer through capillary 105, which buffer flows through porous barrier 110. A detector proximal to particle set 115 is used to detect the added nucleotide, thus detecting the identity and sequencing the template. The steps are repeated, with each cycle identifying at least one nucleotide in the template sequence.

IV. Sequencing by photobleaching

Typically, in sequencing by synthesis a fluorescently labeled nucleotide is detected as it is added to a growing nucleic acid chain, e.g., a primer that is hybridized to a template. As more fluorescently labeled nucleotides are added to the primer strand, the signal level increases and the ability to detect the nucleotide addition decreases. In the present method, fluorescently labeled nucleotides are photobleached after incorporation to reduce the signal level and increase the template nucleic acid read length.

The template is incubated with each different nucleotide in series and as a nucleotide is added to the primer, a signal is detected. For example, a nucleic acid template and primer are anchored or immobilized, e.g., on a membrane or on a capillary or microchannel wall, e.g., through streptavidin-biotin binding. A polymerase and a fluorescent nucleotide or a mixture of fluorescent nucleotides and non-fluorescent nucleotides, e.g., A, G, C, or T, are incubated with the template and primer, e.g., by flowing the nucleotides and polymerase across the immobilized templates or by contacting a membrane with the polymerase and nucleotides. Any of the nucleotides or nucleotide analogs in the present invention are optionally used. Fluorescently labeled nucleotides, e.g., nucleoside-5'-triphosphates with a fluorescent label moiety attached, e.g., to the base, are preferred. If the labeled nucleotide is complementary to the template, it is incorporated into the growing primer. Typically unincorporated nucleotides are removed before detection, e.g., by flowing buffer through the channel or across the membrane. A fluorescent signal is then detected from the incorporated nucleotides or nucleotide analogs. If a nucleotide is not incorporated, a signal is not detected, and the process is repeated with a different nucleotide until the complementary nucleotide is determined. Alternatively, all four nucleotides are added together, e.g., when each nucleotide is labeled with a detectably different fluorescent label.

Each time a fluorescent nucleotide is added to the growing chain, the overall or background level of fluorescence increases, thereby making it more difficult to detect a signal from a newly incorporated nucleotide. For example, to reduce the level of fluorescence and prevent previously incorporated nucleotides from interfering with the signals obtained, the signals are photobleached.

Photobleaching comprises applying a light pulse to the nucleic acid primer into which a fluorescent nucleotide has been incorporated. The light pulse typically comprises a wavelength equal to the wavelength of light absorbed by the fluorescent nucleotide of interest. The pulse is applied for about 50 seconds or less, about 20 seconds or less, about 10 seconds or less, about 5 seconds or less, about 2 seconds or less, about 1 seconds or less, or about 0.1 second or less. The pulse destroys the fluorescence of the fluorescently labeled nucleotides and/or the fluorescently labeled primer or nucleic acid or reduces it to an acceptable level, e.g., a background level or a level that is low enough to prevent signal buildup over several cycles. Background level is typically a signal level over which an additional fluorescent signal due to the incorporation of an additional nucleotide to a growing nucleic acid chain is detectable. The fluorescence does not have to be completely bleached out. In fact, the photobleach pulse is optionally applied for a photobleach half-life, i.e., the time it takes to reduce the fluorescence by one half. If a half-life photobleach time is used, the signal from the first nucleotides to be incorporated will eventually be reduced to background or substantially zero because each subsequent photobleach pulse reduces the remaining fluorescence for another half-life each time a nucleotide is incorporate and photobleached. For example, if the pulse is applied for the bleach time half-life, one half of the fluorescent intensity is bleached out. After three nucleotides or bases are added to the primer, the first fluorescent nucleotide added will have experienced three half-lives, thus reducing the fluorescent intensity of that base by about 95%. After four cycles, the intensity will only be about 99% less than the original level. Therefore, the photobleach pulse need not be applied long enough to completely bleach out the signal.

By continually reducing the fluorescence signal after the addition of nucleotides, longer sequences are optionally sequenced than previously methods have allowed. For example, template nucleic acids of about 100 or more, about 500 or more, about 1000 or more, about 2000 or more, about 10,000 or more, or about 50,000 or more nucleotides are optionally sequenced. Furthermore, since the fluorescence signal is photobleached with each nucleotide addition, with every other nucleotide addition, with every fifth nucleotide addition, or the like, the signal is read with at least about 70% accuracy, at least about 80% accuracy, at least about 90% accuracy, or at least about 95% accuracy even when the nucleic acid template is about 500 or more, about 1000 or more, about 2000 or more, about 10,000 or more, or about 50,000 or more nucleotides in length.

In some embodiments, a build up of fluorescent signal as subsequent nucleotides are added is counteracted by using a combination of fluorescently labeled nucleotides and non-labeled nucleotides. For example a low concentration of labeled nucleotides are added in combination with non-labeled nucleotides, e.g., in a 1/1000 ratio. Therefore, when a nucleotide is added, the small percentage of labeled nucleotides added is detected. The non-labeled nucleotides do not interfere with or contribute to signal buildup but are continuously elongated and available for subsequent additions. The read length for a nucleic acid is thereby extended as in the photobleaching described above.

In other embodiments, non-labeled nucleotides are used in combination with labeled chain terminating nucleotides to increase read length. The eventual read length typically depends on the efficiency with which strands are extended. For example, a 99% efficiency leads to a 64% reduction in signal after 100 cycles. If the incorporation of one fluorescent nucleotide reduces the efficiency of the next nucleotide (natural or fluorescent), then the read length is further compromised. One scheme to decrease the effect of incorporation efficiency after a labeled nucleotide is added is to use strand-terminating nucleotides for the labeled nucleotides and mix them at low concentration with non-labeled, non-terminating nucleotides, e.g., in a 1 to 1000 ratio. Therefore, only a small fraction of primer molecules are labeled and only a small fraction are terminated. The remainder are continuously extended and detected. Therefore, the signal is not reduced and the read length is extended.

V. Sequencing by intercalation

Sequencing by synthesis using intercalating dyes for detection provides a way to measure an increased fluorescent signal whenever a nucleotide is incorporated into a nucleic acid chain, e.g., a primer strand. The template, primer and sequencing reagents, e.g., polymerase and nucleotides, are incubated in the presence of an intercalating dye. When a nucleotide is incorporated into a primer strand, it extends the double-stranded region of the nucleic acid, and the intercalating dye inserts or intercalates into that extended double stranded region. Therefore, whenever a nucleotide is added the signal is increased. Using this method of detection allows naturally-occurring nucleotides, e.g., non-labeled nucleotides, to be used in the synthesis reactions.

A nucleic acid template and primer are hybridized according to procedures well known in the art and as described above, resulting in a double stranded region. For example, a nucleic acid template is attached to a particle array, e.g., comprising ceramic beads. The primer is hybridized to the template strand, forming a double stranded region.

The hybridized template/primer is incubated with one of a series of nucleotides, e.g., A, C, G, T, U, or the like, and an intercalator, e.g., an intercalating dye. The nucleotides are optionally unlabeled nucleotides. For example, incubation optionally occurs by flowing the nucleotides across the particle array or flowing the particle array through the nucleotides. The nucleotides and intercalator are optionally added together or separately. Addition of a nucleotide, e.g., if the nucleotide added is complementary to the template strand, results in an extended double-stranded region and the intercalating dye intercalates or inserts itself into that region. The intercalating dye is then detected to determine if the nucleotide was added. If an increase in intercalation is detected, e.g., by an increase in signal due to an additional intercalating dye molecule in each template/primer strand, a nucleotide was added. If no increase is detected, the nucleotide was not added and the sequence is performed again with a different nucleotide, e.g., until the complementary base is determined. The templates and primers are optionally rinsed after the addition of a nucleotide, thus removing any unincorporated nucleotides from the reaction mixture either before or after detection.

In one embodiment, photobleaching is used, as described above, to photobleach or reduce the fluorescence of the intercalators already present within the double-stranded region. Any added or additional signal detected is indicative of an additional stacked base in a double stranded region. Alternatively, the intercalators remain intercalated into the stacked bases of the template and extended primer and newly incorporated nucleotides are detected by measuring an increase in the fluorescent signal due to added intercalators.

Intercalating dyes typically intercalate into a double helix at the rate of 1 intercalator per about 4 to about 5 bases. However, in the presence of many template/primer molecules and with the random intercalation of the dye, i.e., not specific to any to the sequence, the signal obtained is typically only reduced by a factor of about 5 of the possible signal if every base is intercalated with the dye. This level of intercalation is easily detected, thus providing a new sequencing detection method.

The intercalators of the present invention are typically intercalating dyes including, but not limited to, ethidium, ethidium bromide, an acridine dye, an intercalating nucleic acid stain, a cyanine dye, such as SYBR green, proflavin, propidium iodide, acriflavin, proflavin, actinomycin, anthracyclines, or nogalamycin. The intercalators of the present invention typically comprise a detectable moiety, e.g., a label as described above. For more information on possible intercalators, see, e.g., *Handbook of Fluorescent Probes and Research Chemicals,* Richard Haugland, Sixth Edition, Molecular Probes, Eugene Oregon (1996) and http://www.probes.com/handbook/sections/2300.html (online 1999 version of the *Handbook of Fluorescent Probes and Research Chemicals Sixth Edition* by Molecular Probes, Inc.) (Molecular Probes, 1999).

The intercalating dye is optionally present in the reaction buffer or added to the reaction as needed, e.g., after addition of a nucleotide to the primer. For example in a microfluidic device, an intercalator is optionally flowed across the template/primer molecules by application of pressure or by electrokinetic gradients, e.g., by reverse electrophoresis.

VI. Sequencing a nucleic acid in a microfluidic device

Any of the above sequencing technologies or any other known sequencing techniques are optionally practiced in a microfluidic device, e.g., a microfluidic device comprising bead arrays. The devices are optionally fabricated to comprise nucleotide analogs as described above, as well as other sequencing reagents, such as intercalating dyes, fluorescent nucleotides, phosphate nucleotides, carbamate nucleotides, phosphatases, reducing agents, and the like. The reagents are optionally stored within the reservoirs of the devices, as described below, accessed through a capillary channel, e.g., from a microwell plate, or supplied on particle arrays.

Particle arrays are used, e.g., to immobilize a set of nucleic acid templates for sequencing. The template and/or primer are optionally attached to a set of particles and positioned in or flowed through a microfluidic device. For example, a porous barrier is used to immobilize the particles (comprising nucleic acid templates and primers) within a microfluidic channel. Reagents are then flowed across the particles to contact the template and primer and sequence the nucleic acid template. In addition, used or spent reagents, e.g., unincorporated nucleotides or cleaved blocking groups, are washed from the channel while maintaining the elongated nucleic acid in place, e.g., for another sequencing cycle. Particle arrays are discussed in more detail in U.S. Ser. No. 60/128,643, filed Apr. 9, 1999 and in co-filed application, "Manipulation of Microparticles in Microfluidic Systems," by Mehta et al. Microfluidic devices are descried below and in a number of patents and publications by the inventors and their co-workers. These publications are also described below.

The bead technology useful in the present invention typically uses arrays of particles, e.g., flowed through the channels of a microfluidic device. An "ordered array of a plurality of sets of particles" is an array of particle sets (each particle set is constituted of similar or identical particle "members" or "types") having a spatial arrangement. The spatial arrangement of particle sets can be selected or random. In a preferred embodiment, the spatial arrangement is selected. The arrangement can be known or unknown. In a preferred embodiment, the spatial arrangement of particle sets is known. A "set" of particles is a group or "packet" of particles having similar or identical constituents.

The particles are typically flowed through the capillaries or microfluidic devices of the invention, e.g., to provide sequencing reagents or to contact nucleic acid templates and primers to perform sequencing reactions. A "particle movement region" is a region of a microscale element in which the particles are moved. A "fluid movement region" is a region of a microscale element in which fluidic components are moved. As discussed supra, fluidic and particulate elements are moved by any of a variety of forces, including capillary, pressure, electrokinetic and the like.

A "particle retention region" is a region of a microscale element in which particles can be localized, e.g., by placing a physical barrier or porous matrix within or proximal to the retention region, by application of magnetic or electric fields, by application of pressure, or the like. For example, a porous matrix optionally comprises a fixed set of particles, e.g., 186 $\mu$m particles, within a microchannel.

A train of reagents (i.e., an ordered or semi-ordered arrangement of fluidic reagents in a channel) comprising a plurality of sequencing reagents is flowed across the first set of particles, or the first set of particles is flowed through the reagent train, depending on the application. This results in contacting the at least one set of nucleic acid templates with the plurality of sequencing reagents. Signals resulting from exposure of the first set of particles to the reagent train are selected, thereby providing a portion of sequence of the nucleic acid template. For example, the reagent train can include a polymerase, a sufurylase, an apyrase, an inorganic phosphate, ATP, a thermostable polymerase, luciferin, luciferase, an endonuclease, an exonuclease, $Mg^{++}$, a molecular crowding agent, a buffer, a dNTP, a dNTP analog, a fluorescent nucleotide, a chain terminating nucleotide, a reversible chain terminating nucleotide, a phosphatase, a reducing agent, an intercalator, a salt, DTT, BSA, a detergent (e.g., triton® or tween®), chemicals to inhibit or enhance EO flow (e.g., polyacrylamide), or any other sequencing reagent of interest.

The number of ordered sets constituting the array depends on the selected application. For example, as discussed in more detail herein, one exemplar array for sequencing nucleic acids comprises about 2, 3, or 4 sets of particles (e.g., beads, cells, microspheres, etc.). In other implementations, 5, 10, 50, 100, 500, 1000, 5,000, 10,000, 50,000 or even 100,00 or more different sets of particles can be present in the arrays. The precise number of particles in an array depends on the intended use of the array.

The array components (i.e., particles) of the arrays of the invention can be essentially any discreet material which can be flowed through a microscale system. Example particles include beads and biological cells. For example, polymer beads (e.g., polystyrene, polypropylene, latex, nylon and many others), silica or silicon beads, clay or clay beads, ceramic beads, glass beads, magnetic beads, metallic beads, inorganic compound beads, and organic compound beads can be used. An enormous variety of particles are commercially available, e.g., those typically used for chromatography (see, e.g., the 1999 Sigma "Biochemicals and Reagents for Life Sciences Research" Catalog from Sigma (Saint Louis, Mo.), e.g., pp. 1921–2007; The 1999 Suppleco "Chromatography Products" Catalogue, and others), as well as those commonly used for affinity purification (e.g., Dynabeads™ from Dynal, as well as many derivitized beads, e.g., various derivitized Dynabeads™ (e.g., the various magnetic Dynabeads™, which commonly include coupled reagents) supplied e.g., by Promega, the Baxter Immunotherapy Group, and many other sources).

The array particles can have essentially any shape, e.g., spherical, helical, spheroid, rod-shaped, cone-shaped, cubic, polyhedral, or a combination thereof (of course they can also be irregular, as is the case for cell-based particles). In addition, the particles can be a variety of sizes. Typically, the particles are about 0.1 $\mu$m to about 500 $\mu$m. Alternatively, the particles are about 0.5 $\mu$m to about 50 $\mu$m or about 1 $\mu$m to about 20 $\mu$m. Particles are optionally coupled to reagents, affinity matrix materials, or the like, e.g., nucleic acid synthesis reagents, peptide synthesis reagents, polymer synthesis reagents, nucleic acids, nucleotides, nucleobases, nucleosides, peptides, amino acids, monomers, cells, biological samples, synthetic molecules, or combinations thereof. Particles optionally serve many purposes within the arrays, including acting as blank particles, dummy particles, calibration or marker particles, capture devices for low concentration reagents, sample particles, reagent particles and test particles.

The particles within the arrays of the invention can present a solid or semi-solid surface for any of a variety of linking chemistries, allowing the incorporation of biological and chemical components of interest into the particle members of the arrays. A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include papers, ceramics, such as glass, metals, metalloids, semiconductive materials, cements, or the like. In addition, substances that form gels, such as proteins (e.g., gelatins), lipopolysaccharides, silicates, agarose and are also optionally used.

A wide variety of linking chemistries are available for linking molecules to a wide variety of solid or semi-solid particle support elements. These chemistries can be performed in situ (i.e., in the microfluidic system, by flowing appropriate reagents, e.g., nucleic acids, proteins, and samples present in low concentrations, into contact with the particles, or vice-versa), or outside of a microfluidic environment, e.g., prior to introduction of the particles into the microfluidic system. It is impractical and unnecessary to describe all of the possible known linking chemistries for linking molecules to a solid support. It is expected that one of skill can easily select appropriate chemistries, depending on the intended application.

In one preferred embodiment, the particles of the invention comprise silicate elements (e.g., glass or silicate beads). An array of silicon-based molecules appropriate for functionalizing surfaces are commercially available. See, for example, Silicon Compounds Registry and Review, United Chemical Technologies, Bristol, Pa. Additionally, the art in this area is very well developed and those of skill will be able to choose an appropriate molecule for a given purpose. Appropriate molecules can be purchased commercially, synthesized de novo, or it can be formed by modifying an available molecule to produce one having the desired structure and/or characteristics.

The substrate linker attaches to the solid substrate through any of a variety of chemical bonds. For example, the linker is optionally attached to the solid substrate using carbon-carbon bonds, for example via substrates having (poly) trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups. The particular linking group is selected based upon, e.g., its hydrophilic/hydrophobic properties where presentation of an attached polymer in solution is desirable. Groups which are suitable for attachment to a linking group include amine, hydroxyl, thiol, carboxylic acid, ester, amide, isocyanate and isothiocyanate. Preferred derivatizing groups include aminoalkyltrialkoxysi lanes, hydroxyal kyltrialkoxysilanes, polyethyleneglycols, polyethyleneimine, polyacrylamide, polyvinylalcohol and combinations thereof.

VII. Integrated Systems and Kits

The microfluidic devices of the present invention are used to perform sequencing by incorporation or sequencing by synthesis. The devices generally comprise a body structure with microscale channels or other cavities fabricated therein. Typically, the device includes reagent sources, a main channel, and a detection region. For example, to sequence a nucleic acid, templates and primers are typically flowed through a main channel of a microfluidic device and immobilized within the channel. Alternatively, microfluidic devices are provided with templates and primers immobilized therein. Sequencing reagents, e.g., polymerases and nucleotides, are flowed from reagent sources, e.g., reservoirs or microwell plates, to contact the template and primer. Complementary nucleotides are incorporated and detected, e.g., in a detection region proximal to the immobilized templates and primers. The steps are iteratively repeated to provide, e.g., an entire template sequence or portion thereof.

For example, a device typically comprises a main channel, which main channel comprises the template and primer, e.g., on a particle array. The main channel typically comprises a particle retention region and a flow region. For example a particle array is fixed in the main channel in the particle retention region and reagents are flowed through the flow region and across the particle array to sequence a nucleic acid template. For example, FIG. 1 provides a particle array stacked or fixed in a microscale channel, e.g., by a porous matrix. Reagents are flowed through the channel and across the particle array. Unincorporated nucleotides are optionally washed out of the channel, e.g., through the porous matrix. The main channel or microscale cavity is used, e.g., to mix or incubate two or more reagents, to react two or more reagents, to dilute reagents, to separate various components, and the like. Typically, the reservoirs or sources of reagents are fluidly coupled to the main channel so that reagents are optionally introduced into the main channel from the reservoirs.

Reagent sources are typically fluidly coupled to the main channel. The reagent sources are typically reservoirs or wells fluidly coupled to the main channel for adding, removing, or storing the various reagents of interest, e.g., sequencing reagents. Alternatively, the reagent source comprises a sipper capillary fluidly coupled to the main channel and to a reagent source, e.g., a microwell plate. A train of reagents is optionally stored in a microwell plate which is then accessed by the sipper capillary for addition into the device.

A detection region is typically included in the devices of the present invention for the detection of labeled compounds. For example, the nucleic acids are optionally flowed through a detection region, e.g., a region of the main channel, after addition of a nucleic acid. Alternatively, the nucleic acids, e.g., attached to particle arrays, are fixed in the channel within the detection region.

The detection region is optionally a subunit of a channel, or it optionally comprises a distinct channel that is fluidly coupled to the plurality of channels in the microfluidic device, e.g., to the main channel. The detection region typically includes a window at which a signal is monitored. The window typically includes a transparent cover allowing visual or optical observation and detection of the assay results, e.g., observation of a calorimetric or fluorometric signal or label. Examples of suitable detectors are well known to those of skill in the art and are discussed in more detail below.

The above channel regions are fluidly coupled to each other and to various pressure sources and/or electrokinetic sources. Fluidic materials, such as polymerase solutions, nucleotides, reducing agents, sequencing reagents, and the like, are typically transported through the interconnected channel system by the application of pressure and/or electrokinetic forces to the fluid materials in the channels.

Therefore, various pressure sources and electrokinetic controllers are optionally coupled to the devices of the invention.

Typically, the pressure sources are applied at channel ends. For example a waste well is optionally placed at one end of a main channel with a sample source at the other end. A pressure source applied at the waste well is optionally used to draw fluid into the channel. For example, a vacuum source may be fluidly coupled to the device at a waste reservoir located at the end of the main channel. The vacuum optionally draws any excess, or unused material, e.g., unincorporated nucleotides, into the waste reservoir to which the vacuum source is fluidly coupled. For example the vacuum pulls fluid through a porous matrix into a waste reservoir. Alternatively, a positive pressure source is fluidly coupled to a sample well or reservoir at one end of a main channel. The pressure then forces the material into and through the main channel. The vacuum source draws fluid into the main channel for mixing or reacting with other reagents.

Alternatively, electrokinetic forces, e.g., high or low voltages, are applied at reservoirs to introduce materials into the channels or transport materials through the channels. For example, voltage gradients applied across a separation channel are used to move fluid down the channel, thus separating the components of the material as they move through the channel at different rates. In other embodiments, centrifugal force is used to flow reagents through channels.

One embodiment of the present devices is illustrated in FIG. 1. As shown, the system comprises main channel 105, which is optionally a capillary or a channel in a microfluidic device. To sequence a nucleic acid, various reagents are added into main channel 105. For example, a template and primer are introduced into main channel 105 from a microwell plate. The template and primer are then captured and retained by particle set 115, which is held in place by particle retention element 110. Other reagents used in the sequencing are introduced into main channel 105 also. For example, a polymerase solution and a mixture of nucleotides are introduced into main channel 102 from, e.g., a microwell plate or a reservoir located within the microfluidic device. In the presence of the polymerase, one or more nucleotides are added to the nucleic acid primer to form an extended nucleic acid. Unincorporated nucleotides are washed from the channel, e.g., flowed through porous particle retention element 110. The newly incorporated nucleotides are detected, e.g., by fluorescence detection, by a detector positioned proximal to particle set 115.

Figure 8:
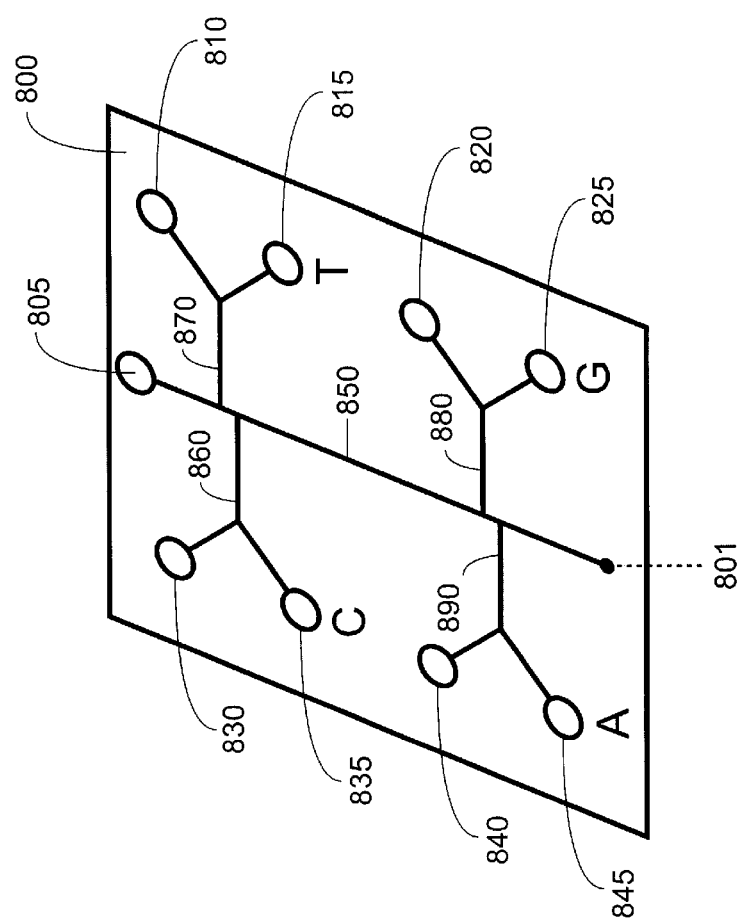
FIG. 8: Schematic of a microfluidic device useful in sequencing by synthesis.

In another embodiment, nucleic acids are sequenced in a multi-channel device 800 as shown in FIG. 8. For example, template and primer are loaded into main channel 850 through sipper capillary 801, e.g., using pressure control at the sipper and/or wells 810–845. Nucleotides and buffer are stored, e.g., in reagent wells 810–845, and sequentially introduced into main channel 850. For example, dATP is flowed from well 845 into channel region 890 and then into main channel 850, e.g., adding dATP to the primer strand if it is complementary to the template. The channel is then rinsed with buffer, e.g., from well 840, to remove unincorporated dATP, e.g., into waste well 805. The remaining nucleotides, e.g., dCTP, dTTP, and dGTP, are added in the same sequential manner, e.g., until the template or a desired portion thereof is sequenced. For example, wells 810–835 are optionally used to add the remaining nucleotides, through channel regions 860–880, into main channel 850 to contact the template and primer.

In some embodiments, one or more of the components are attached to one or more sets of particles, which are flowed through the device in the same manner. For example, in a preferred embodiment, the template and primer are typically attached to a set of particles which is flowed into main channel 850 and immobilized therein. The nucleotides and buffers are flowed across the set of particles and unincorporated nucleotides are removed, e.g., into waste well 805. A detector is optionally placed proximal to main channel 850 to detect incorporated nucleotides. Any of the above described sequencing by synthesis methods are optionally performed in this manner.

Although the devices and systems specifically illustrated herein are generally described in terms of the performance of a few or one particular operation, e.g., a sequencing using particle arrays, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components, or the like. The devices and systems used for the above assays are described below.

Microfluidic devices generally

A variety of microscale systems are optionally adapted to the present invention by incorporating particle arrays, polymerases, templates, primers, sequencing reagents, and the like. A variety of microfluidic devices are optionally adapted for use in the present invention, e.g., by designing and configuring the channels as discussed below. The inventors and their co-workers have provided a variety of microfluidic systems in which the arrays of the invention can be constructed and sequencing reactions carried out. For example, Ramsey WO 96/04547 provides a variety of microfluidic systems. See also, Ramsey et al. (1995), Nature Med. 1(10): 1093–1096; Kopf-Sill et al. (1997) "Complexity and performance of on-chip biochemical assays," SPIE 2978:172–179 February 10–11; Bousse et al. (1998) "Parallelism in integrated fluidic circuits," SPIE 3259:179–186; Chow et al. U.S. Pat. No. 5,800,690; Kopf-Sill et al. U.S. Pat. No. 5,842,787; Parce et al., U.S. Pat. No. 5,779,868; Parce, U.S. Pat. No. 5,699,157; U.S. Pat. Nos. 5,852,495 (J. Wallace Parce) issued Dec. 22, 1998; 5,869,004 (J. Wallace Parce et al.) issued Feb. 9, 1999, 5,876,675 (Colin B. Kennedy) issued Mar. 2, 1999; 5,880,071 (J. Wallace Parce et al.) issued Mar. 9, 1999; 5,882,465 (Richard J. McReynolds) issued Mar. 16, 1999; 5,885,470 (J. Wallace Parce et al.) issued Mar. 23, 1999; 5,942,443 (J. Wallace Parce et al.) issued Aug. 24, 1999; 5,948,227 (Robert S. Dubrow) issued Sep. 7, 1999; 5,955,028 (Calvin Y. H. Chow) issued Sep. 21, 1999; 5,957,579 (Anne R. Kopf-Sill et al.) issued Sep. 28, 1999; 5,958,203 (J. Wallace Parce et al.) issued Sep. 28, 1999; 5,958,694 (Theo T. Nikiforov) issued Sep. 28, 1999; and 5,959,291 (Morten J. Jensen) issued Sep. 9, 1928/199; Parce et al. WO 98/00231; Parce et al. WO 98/00705; Chow et al. WO 98/00707; Parce et al. WO 98/02728; Chow WO 98/05424; Parce WO 98/22811; Knapp et al., WO 98/45481; Nikiforov et al. WO 98/45929; Parce et al. WO 98/46438; Dubrow et al., WO 98/49548; Manz, WO 98/55852; WO 98/56505; WO 98/56956; WO 99/00649; WO 99/10735; WO 99/12016; WO 99/16162; WO 99/19056; WO 99/19516; WO 99/29497; WO 99/31495; WO 99/34205; WO 99/43432; and WO 99/44217; U.S. Pat. No. 5,296,114; and e.g., EP 0 620 432 A1; Seiler et al. (1994) Mitt Gebiete Lebensm. Hyg. 85:59–68; Seiler et al. (1994) Anal. Chem. 66:3485–3491; Jacobson et al. (1994) "Effects of Injection Schemes and Column Geometry on the Performance of Microchip Electrophoresis Devices" Anal. Chem. 66: 66. 1107–1113; Jacobsen et al. (1994)."Open Channel Electrochromatograpy on a Microchip" Anal. Chem. 66:2369–2373; Jacobsen et al. (1994) "Precolumn Reactions with Electrophoretic Analysis Integrated on Microchip" Anal. Chem. 66:4127–4132; Jacobsen et al. (1994) "Effects of Injection Schemes and Column Geometry on the Performance of Microchip Electrophoresis Devices." Anal. Chem. 66:1107–1113; Jacobsen et al. (1994) "High Speed Separations on a Microchip." Anal. Chem. 66:1114–1118; Jacobsen and Ramsey (1995) "Microchip electrophoresis with sample stacking" Electrophoresis 16:481–486; Jacobsen et al. (1995) "Fused Quartz Substrates for Microchip Electrophoresis" Anal. Chem. 67: 2059–2063; Harrison et al. (1992) "Capillary Electrophoresis and Sample Injection Systems Integrated on a Planar Glass Chip." Anal. Chem. 64:1926–1932; Harrison et al. (1993) "Micromachining a Miniaturized Capillary Electrophoresis-Based Chemical Analysis System on a Chip." Science 261: 895–897; Harrison and Glavania (1993) "Towards Miniaturized Electrophoresis and Chemical System Analysis Systems on Silicon: An Alternative to Chemical Sensors." Sensors and Actuators 10:107–116; Fan and Harrison (1994) "Micromachining of Capillary Electrophoresis Injectors and Separators on Glass Chips and Evaluation of Flow at Capillary Intersections. Anal. Chem. 66: 177–184; Effenhauser et al. (1993) "Glass Chips for High-Speed Capillary Electrophoresis Separations with Submicrometer Plate Heights" Anal. Chem. 65:2637–2642; Effenhauser et al. (1994) "High-Speed Separation of Antisense Oligonucleotides on a Micromachined Capillary Electrophoresis Device." Anal. Chem. 66:2949–2953; and Kovacs EP 0376611 A2.

The above devices, systems, features, and components are used in the integrated systems described below, e.g., to sequence nucleic acids.

For example, the channel 105 in FIG. 1 is optionally used to sequence a nucleic acid by synthesis. A set of templates and/or primers is attached to particle set 115 and flowed through or positioned within channel 105. Particle retention element 110 is optionally used to immobilize particle set 115 comprising the templates and primers. Alternatively, particle set 115 is held in place by magnetic force or chemically attached to the surface of channel 105. Sequencing reagents are typically flowed across particle set 115. For example, dATP, dGTP, dTTP, and dCTP, e.g., each comprising a reversible chain terminating blocking group and labeled with a distinguishable fluorescent label are flowed through channel 105 to contact the template and primer on particle set 115. A nucleotide is incorporated into the primer, e.g., a nucleotide that is complementary to the template nucleic acid, and detected. For example, unincorporated nucleotides are removed from the channel, e.g., by flowing buffer through the channel, and the identity of the incorporated nucleotide is determined based on the fluorescent signal measured, e.g., by a detector positioned proximal to particle set 115. Reagents are then flowed through channel 105 to remove the 3'-blocking groups so that additional nucleotides are incorporated into the primer nucleic acid. For example, a reducing agent and/or a phosphatase is flowed through channel 105 to remove a phosphate blocking group. Alternatively, the blocking groups are removed prior to detection and detection occurs downstream of particle retention element 110, e.g., as the removed and labeled blocking groups are flowed through the porous barrier formed by particle retention element 110.

Figure 6:
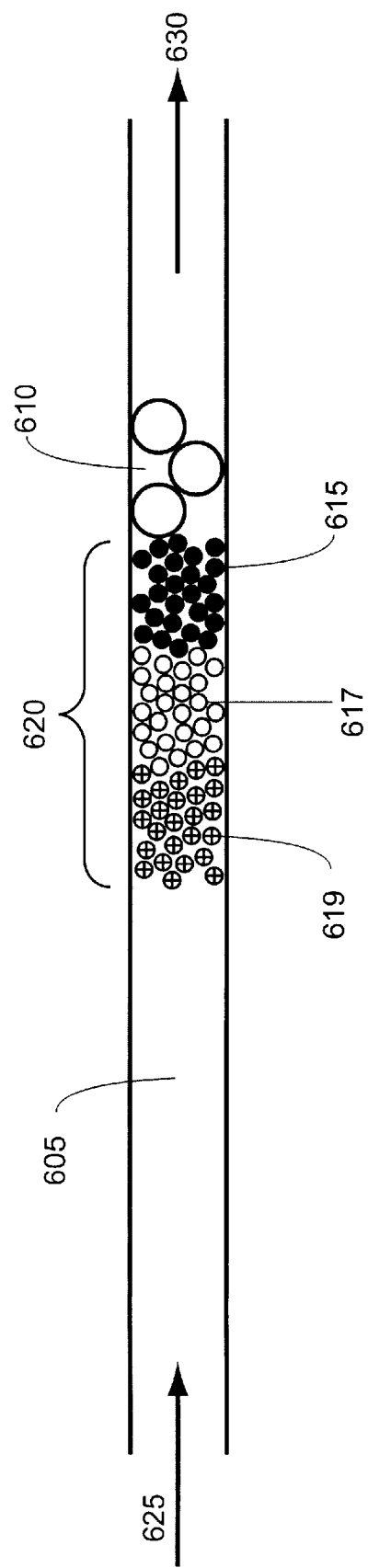
FIG. 6: Side view schematic of a capillary or microchannel comprising an integral or formed porous barrier made from a set of particles. The porous barrier is used, e.g., to capture multiple packets, i.e., sets of particles.

In another embodiment, multiple particle sets are used in a microfluidic channel to sequence one or more nucleic acid template by synthesis. FIG. 6 illustrates capillary 605 comprising multiple particle sets 615, 617, and 619. In addition, particle retention element 610 optionally comprises an immobilized particle set. In one aspect, each of particle sets 615–619 comprises a different nucleic acid template. Reagents are optionally flowed through the channel as described above, thereby sequencing each nucleic acid template, or the nucleotides are flowed through the channel in series. For example, fluorescent dCTP is optionally flowed through channel 605 and incubated with the template/primer nucleic acids. A buffer is typically flowed through the channel to remove any unincorporated dCTP. Any incorporated dCTP remains in the channel as part of the primer strand that is attached to immobilized particle set 615, 617, or 619. Any incorporated dCTP is then detected. For example, a detector is placed proximal to each of the particle sets or a single detector scans across each particle set to detect any incoporated dCTP. The procedure is then repeated as each nucleotide of interest is flowed across particle sets 615–619 to determine the next nucleotide in the template sequence.

In some embodiments reagents are also optionally associated with or attached to a particle set. The reagents are optionally brought into contact with templates and/or primers, e.g., templates and primers immobilized on capillary or channel or walls, and removed from the particles, e.g., by washing or by chemical cleavage. Once removed from the particle set, reagents, e.g., nucleotides are optionally incorporated into the templates.

Figure 5:
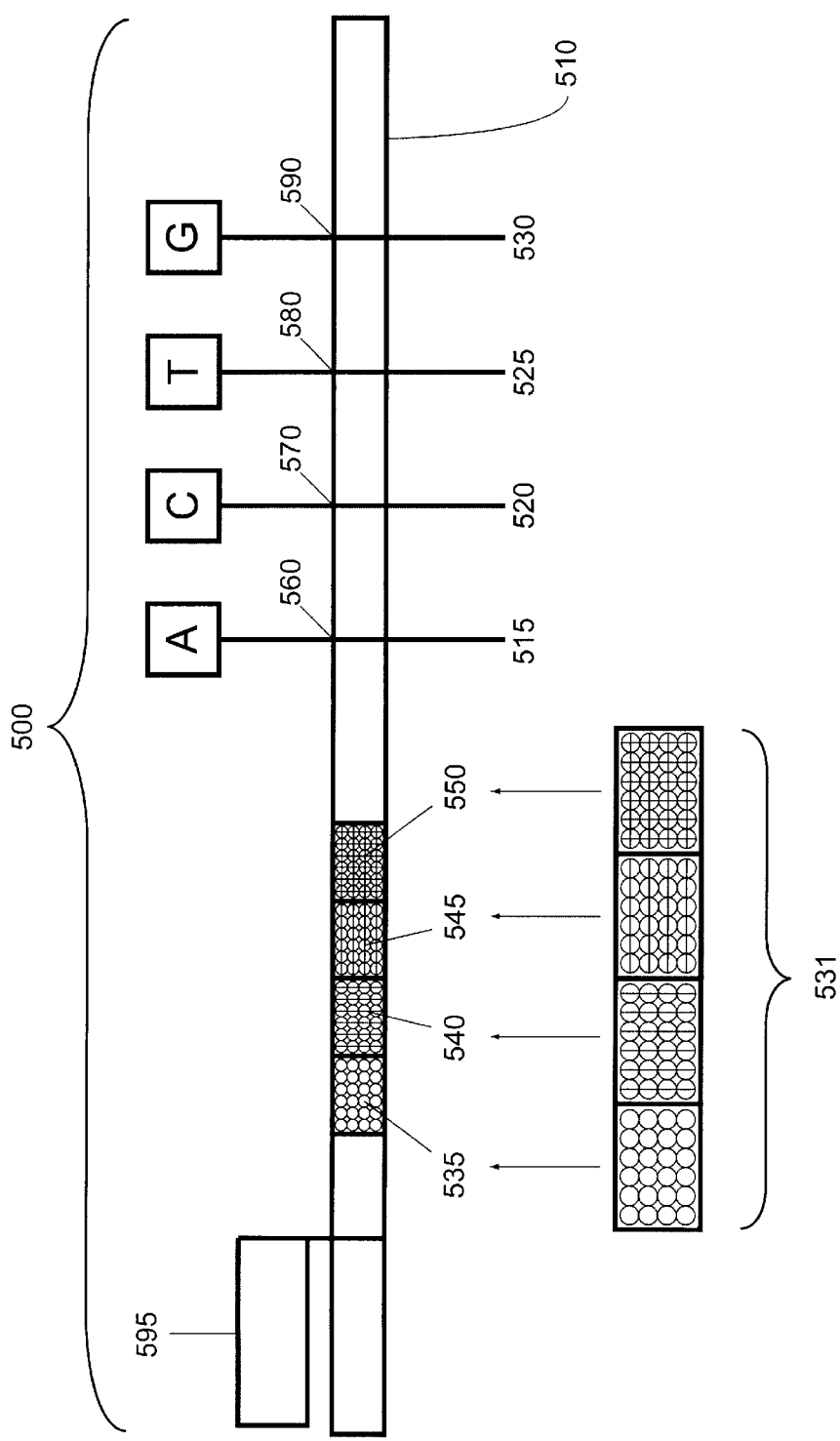
FIG. 5: Side-view schematic of a main channel with reagent introduction channels for sequencing nucleic acids.

In another embodiment, hybridized template/primer sequences are immobilized onto particle sets that are then flowed through various reagents as illustrated by FIG. 5. Microfluidic device 500 comprises main channel 510 and reagent introduction channels 515–530 (as depicted, these are coupled to reagents for separate sequencing reactions, e.g., comprising A, G, C, or T nucleotides). Sample train 531 comprising a plurality of samples, e.g., particle sets 535–550, is passed back and forth through intersections 560–590. Reagent from channels 515–530 is flowed across each sample (or selected samples) in train 531 as the train passes the corresponding coupled intersection.

Figure 7:
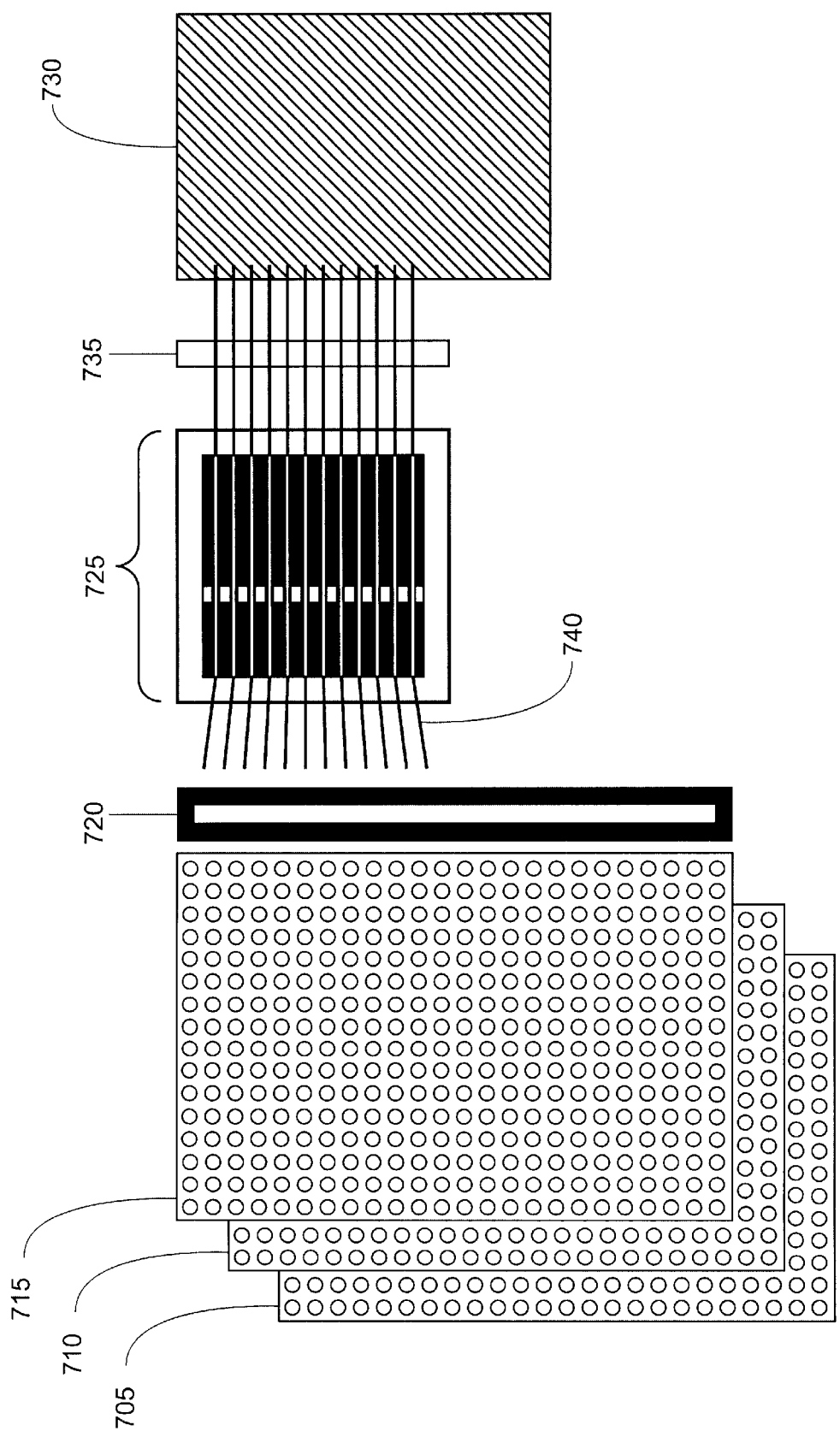
FIG. 7: Schematic illustration of sequencing by synthesis in a high throughput system.

A number of capillaries or channels as described above are optionally banked together, e.g., as parallel channels in a microfluidic device, to provide a high throughout system for sequencing nucleic acids. A schematic of such a system is provided in FIG. 7. FIG. 7 shows a plurality of microtiter plates, e.g., plates 705, 710, and 715. Each well contains a set of particles comprising a nucleic acid template. Therefore, the system shown optionally comprises a plurality of different nucleic acid templates, e.g., about 500 or more, about 1000 or more, or the like, that are optionally sequenced in a high throughput manner. Additional microwell plates and channels are optionally used to provide a greater number of templates. A plate of blank particle sets is also optionally included, e.g., plate 720. The particle sets are loaded into a set of capillaries or channels as shown by channel set 725. The capillaries optionally comprise capillaries or channels as shown in FIG. 1, FIG. 5, FIG. 6, or the like. Multiple particle sets are flowed through each channel and sequenced. For example, 96 particle sets are optionally loaded into each of 12 channels using 12 sipper capillaries, e.g., capillary set 740, or one sipper capillary fluidly coupled to each of the 12 channels. The particle sets are typically retained in the capillary or microchannel by a porous particle retention element, e.g., a sintered glass frit, a set of epoxy coated particles, a constricted channel region, or the like. The particle retention element fixes or retains the particle sets, e.g., particle sets comprising nucleic acid templates, in the channel. The particle sets, e.g., templates, are then optionally exposed to a series or train of reagents. The reagents are typically added through each channel, e.g., from another set of microwell plates, to perform various assays, e.g., sequencing. A single controller, e.g., controller 730 is optionally used to control fluid flow through sipper set 740 and channel set 725. One or more detector is used to monitor the particle packets in the channels as various nucleotides are added. Alternatively, detectors are positioned downstream of the channels to monitor the waste products, e.g., to detect a fluorescent label that has since been washed from the channels. For example, detection optionally occurs in detection region 735. Using a system such as that shown in FIG. 7, one particle set is optionally loaded in about one minute. Therefore 96 templates are optionally analyzed, e.g., sequenced, in 1.6 hours. Alternatively, particles with different chemistries are arrayed sequentially in a single capillary and a template is flowed across the array, e.g., for sequencing.

Instrumentation

In the present invention, materials such as enzymes, nucleic acids, nucleotides, and nucleotide analogs, are optionally monitored and/or detected so that presence of a product of interest can be detected or an activity or concentration can be determined. For example, in a sequencing reaction, one or more nucleotides are added to a growing nucleic acid chain. The nucleotides are typically detected as they are added to the chain when sequencing by synthesis. Therefore, the nucleotides or nucleotide analogs are typically labeled as described above and detected using the instrumentation and integrated systems described below. In some embodiments, the nucleotides are not labeled and labeled intercalating dyes are used to detect addition of nucleotides. Depending on the label signal measurements, decisions are optionally made regarding subsequent fluidic operations, e.g., whether to add a different nucleotide. For example, in some sequencing embodiments, a series of labeled nucleotides, e.g., ATP CTP, GTP, and TTP, is incubated with the template. The template is contacted with a first nucleotide and unincorporated nucleotides are washed from the reaction mixture. If the nucleotide was added to the chain, it is detected. If the nucleotide was not added, no signal is detected. If the signal was detected, then the series of nucleotides begins again. If the nucleotide was not added, then the next nucleotide in the series is added until the identity of that position in the template is determined.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Fluid Direction System

A variety of controlling instrumentation is optionally utilized in conjunction with the microfluidic devices described above, for controlling the transport and direction of fluidic materials and/or materials within the devices of the present invention, e.g., by pressure-based, electrokinetic, magnetic, or centrifugal control or combinations thereof. For example electrophoretic control systems are used to transport particle arrays and reagents through various channel regions. Alternatively, magnetic filed are used to transport magnetic beads or particle arrays, e.g., magnetic beads comprising sequencing reagents.

In the present system, the fluid direction system controls the transport, flow and/or movement of a template, a primer, a particle array, a series of nucleotides, or the like, through the microfluidic device. For example, the fluid direction system optionally directs the movement of a template and a primer through a main channel, in which the template and primer are incubated and hybridized. Sequencing reagents are also optionally added, e.g., buffers, salts, nucleotides, enzymes, and the like. The reagents mix and/or react with the template and the primer in the main channel.

In general, nucleic acids, particle arrays, nucleotides, and other components can be flowed in a microscale system by electrokinetic (including either electroosmotic or electrophoretic) techniques, and/or using pressure-based flow mechanisms, or combinations thereof.

Electrokinetic material transport systems or electrokinetic controllers are used in the present invention to provide movement of particle arrays and sequencing reagents through microfluidic channels. "Electrokinetic material transport systems," as used herein, include systems that transport and direct materials within a microchannel and/or microchamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of proteins, enzymes, peptides, modulators, etc. suspended within the fluid. Similarly, the components, e.g., proteins, peptides, amino acids, enzymes, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis.

Typically, the electrokinetic material transport and direction systems of the invention rely upon the electrophoretic mobility of charged species within the electric field applied to the structure. Such systems are more particularly referred to as electrophoretic material transport systems. For example, in the present system separation of a mixture of components into its individual components typically occurs by electrophoretic separation. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material that alters the surface charge of the channel.

A variety of electrokinetic controllers and systems which are optionally used in the present invention are described, e.g., in U.S. Pat. No. 5,858,195, by Ramsey issued Jan. 12, 1999, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled products in one or more channels toward a detection region or waste reservoir.

Other methods of transport are also available for situations in which electrokinetic methods are not desirable. For example, sample introduction and reaction are best carried out in a pressure-based system to avoid electrokinetic biasing during sample mixing and high throughput systems typically use pressure induced sample introduction. Pressure based flow is also desirable in systems in which electrokinetic transport is also used. For example, pressure based flow is optionally used for introducing and reacting reagents in a system in which the products are electrophoretically separated.

Pressure can be applied to microscale elements, e.g., to a channel, region, or reservoir, to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe, or the like, to displace liquid and thereby raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In some embodiments, a vacuum source is applied to a reservoir or well at one end of a channel to draw a fluidic material through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357. A vacuum applied to a main channel is optionally used to drive fluid flow. For example, a vacuum is used to draw fluid, e.g., unincorporated nucleotides, through a porous barrier and into a waste reservoir.

Hydrostatic, wicking and capillary forces are also optionally used to provide fluid pressure for continuous fluid flow of materials such as enzymes, substrates, modulators, or protein mixtures. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure. The capillary forces are optionally used in conjunction with the electrokinetic or pressure-based flow in the present invention. The capillary action pulls material through a channel. For example a wick is optionally added to, e.g., main channel 105, to aid fluid flow by drawing the reactants and/or products, e.g., unincorporated nucleotides, through the channel, e.g., toward a waste reservoir.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al., Ser. No. 09/310,027. In brief, adsorption of cells, components, proteins, enzymes, and other materials to channel walls or other microscale components during pressure-based flow can be reduced by applying an electric field such as an alternating current to the material during flow.

Mechanisms for focusing labeling reagents, enzymes, modulators, and other components into the center of microscale flow paths, which is useful in increasing assay throughput by regularizing flow velocity, e.g., in pressure based flow, is described in "FOCUSING OF MICROPARTICLES IN MICROFLUIDIC SYSTEMS" by H. Garrett Wada et al. U.S. Ser. No. 60/134,472, filed May 17, 1999. In brief, sample materials are focused into the center of a channel by forcing fluid flow from opposing side channels into the main channel comprising the cells, or by other fluid manipulations.

In an alternate embodiment, microfluidic systems can be incorporated into centrifuge rotor devices, which are spun in a centrifuge. Fluids and particles travel through the device due to gravitational and centripetal/centrifugal pressure forces. For example, unincorporated nucleotides are optionally removed from a set of particles comprising a nucleic acid template and primer using centrifugal force.

In addition to transport through the microfluidic system, the invention also provides for introduction of sample or reagents, e.g., enzymes, nucleotides, nucleic acids, particle sets, and the like, into the microfluidic system. Sources of samples, mixtures of components, and reagents, e.g., enzymes, substrates, labeling reagents, and the like, are fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

Alternative sources include a well disposed on the surface of the body structure comprising the template, primer, sequencing reagent, or the like, a reservoir disposed within the body structure comprising the nucleic acid sample or template, sequencing reagents; a container external to the body structure comprising at least one compartment comprising a template, primer, sequencing reagent, particle set, or the like, or a solid phase structure comprising the template, primer, sequencing reagents, particle sets, or the like in lyophilized or otherwise dried form.

A loading channel region is optionally fluidly coupled to a pipettor channel with a port external to the body structure.

The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic system of the invention optionally includes a very wide variety of storage elements for storing samples and reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system. Such reagents include, but are not limited to, labeling reagents, e.g., enzymes, e.g., phosphatases and polymerases, sequencing reagents, nucleic acids, primers, and the like.

Typically, the fluid controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

Detection System

The devices herein optionally include signal detectors, e.g., which detect fluorescence, phosphorescence, radioactivity, pH, charge, absorbance, luminescence, temperature, magnetism, color, or the like. Fluorescent detection is especially preferred. For example, nucleotides that have been added to a growing chain of nucleotides are optionally detected by fluorescent photobleaching The detector(s) optionally monitors one or a plurality of signals from the nucleic acid template, which is typically immobilized in a microfluidic channel or capillary. For example, the detector optionally monitors an optical signal that corresponds to a labeled component, such as a labeled nucleotide, e.g., that has been added to a template immobilized in a channel. For example, in FIG. 1, templates and primers are typically attached to particle set 115, which is immobilized in channel 105 using particle retention element 110. A detector placed proximal to particle set 115, detects each nucleotide as it is incorporated into the nucleic acid chain.

In another embodiment, a nucleotide is added to a growing chain and a labeled 3'-blocking group is removed from the chain to allow for further elongation. Detection optionally occurs before or after removal of the 3'-blocking group. For example, a 3'-blocking group is optionally removed and then detected as it is flowed to a waster reservoir in a microfluidic device.

A detector is placed proximal to a detection region, e.g., proximal to the immobilized nucleic acid templates and primers, and the labeled components are detected as they bond to the primer. Alternatively, the detector moves relative to the device to determine the position of a labeled nucleotide, or the like (or, the detector can simultaneously monitor a number of spatial positions corresponding to channel regions, e.g., as in a CCD array).

The detector optionally includes or is operably linked to a computer, e.g., which has software for converting detector signal information into sequencing result information, e.g., concentration of a nucleotide, identity f a nucleotide, sequence of the template nucleotide, or the like. In addition, sample signals are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other detection region). Once detected, the flow rate and velocity of materials in the channels is also optionally measured and controlled.

Particularly preferred detection systems of the present invention are optical detection systems for detecting an optical property of a material within the channels and/or chambers of the microfluidic provided herein. Such optical detection systems are typically placed adjacent to a microscale channel of a microfluidic device, and are in sensory communication with the channel via an optical detection window that is disposed across the channel or chamber of the device. For example a detector is optionally placed proximal to a particle set comprising the nucleic acid template and primer of interest, e.g., to detect incorporation of additional nucleotides into the primer.

Optical detection systems include systems that are capable of measuring the light emitted from material within the channel, the transmissivity or absorbance of the material, as well as the materials' spectral characteristics. In preferred aspects, the detector measures an amount of light emitted from the material, such as from a fluorescent or chemiluminescent material, e.g., the labeled products described above. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials, e.g., labeled nucleotides, the detector typically includes a light source which produces light at an appropriate wavelength for activating the fluorescent material, as well as optics for directing the light source through the detection window to the product contained in the channel or chamber. The light source can be any number of light sources that provides an appropriate wavelength, including lasers, laser diodes and LEDs. Other light sources are required for other detection systems. For example, broad band light sources are typically used in light scattering/transmissivity detection schemes, and the like. Typically, light selection parameters are well known to those of skill in the art.

Similar light sources are also used to provide light of appropriate wavelength for photobleaching as described above. In some embodiments, the same light source is used to detect and photobleach the labeled nucleotides that are added to a growing nucleic acid chain.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer. For example, the controller typically controls the length of a photobleaching pulse.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software optionally directs the fluid direction system to transport one or more nucleotides into a main channel, one or more template and primer into a main channel, and any other movement necessary to analyze the results of the assay performed.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages; and the like. For example, the voltages on an electrophoretic separation channel are optionally adjusted.

Figure 2C:
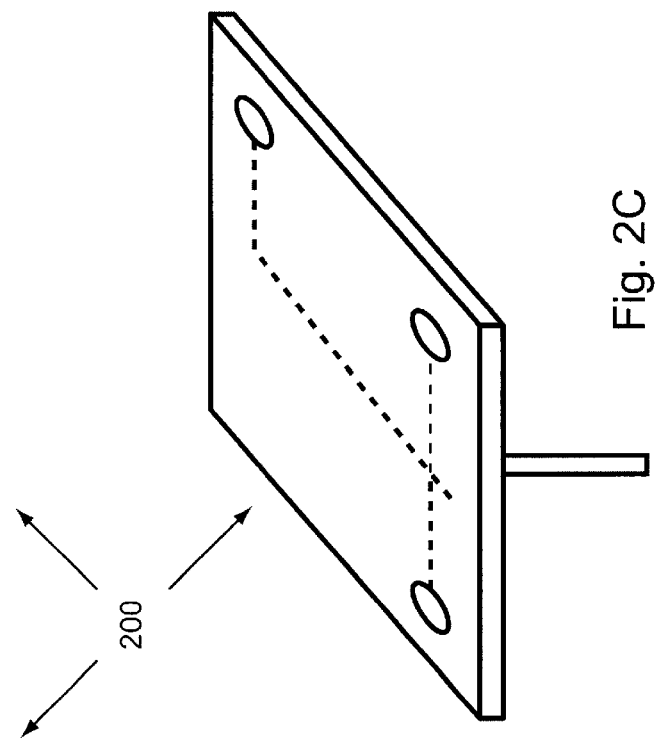
Figure 2A:
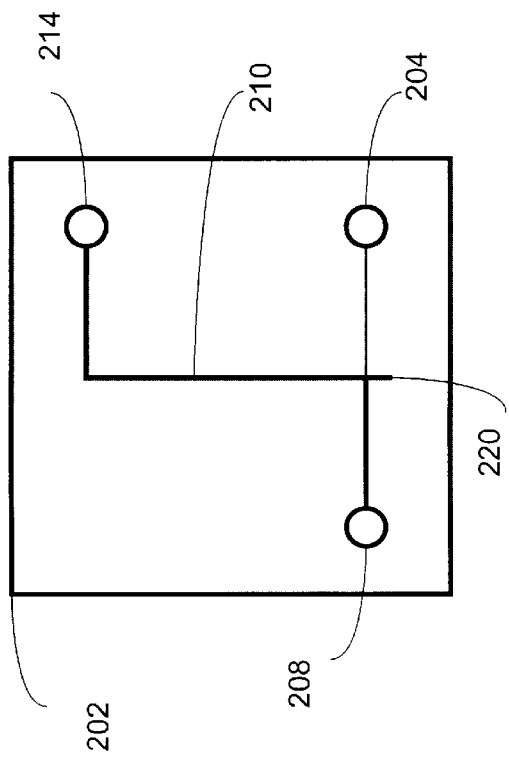
Figure 3:
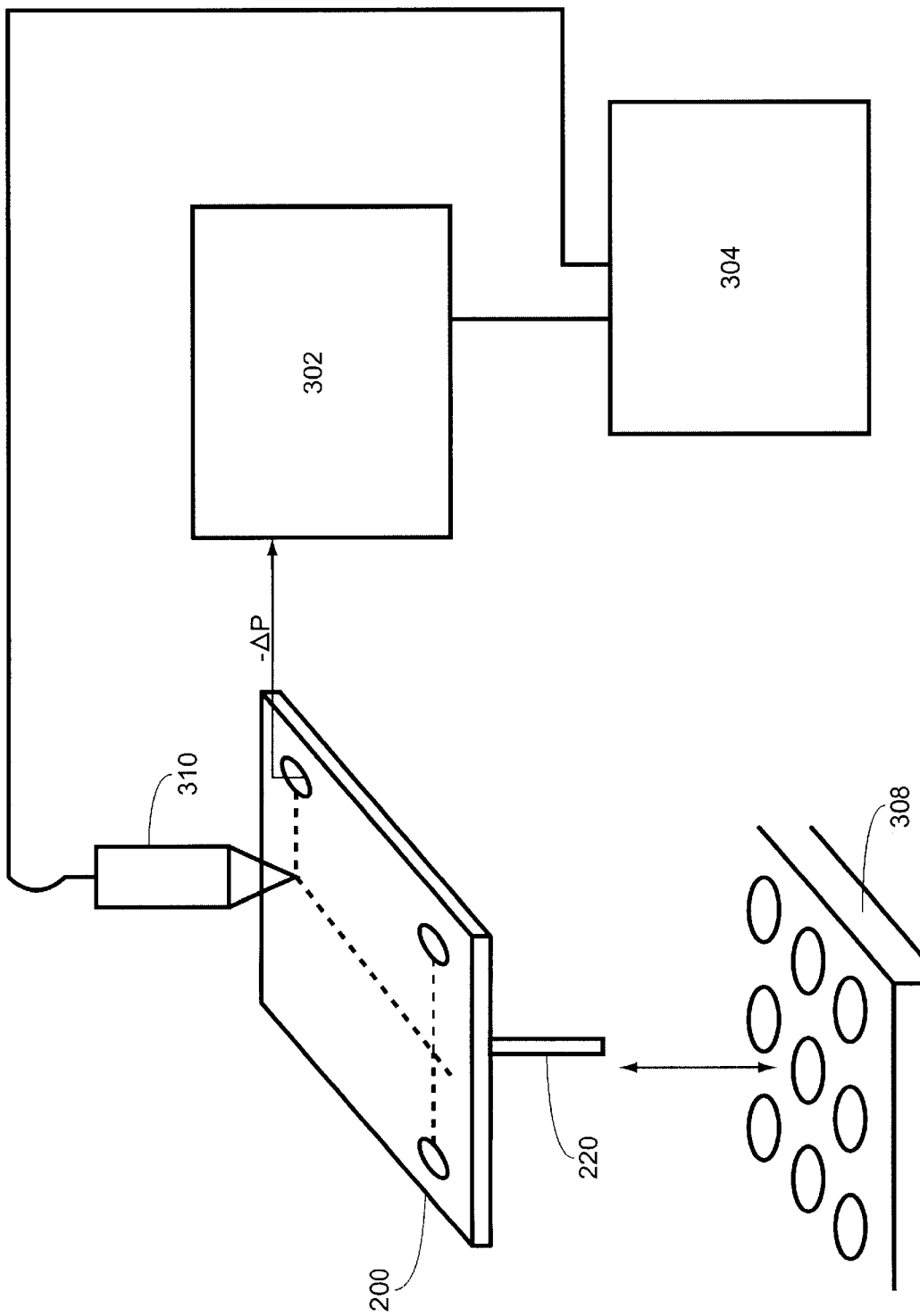
FIG. 3: Schematic drawing of an integrated system of the invention further depicting incorporation of a microwell plate, a computer, detector and a fluid direction system. The integrated system is optionally used with any suitable microfluidic device.

In addition, the computer optionally includes software for deconvolution of the signal or signals from the detection system. For example, a deconvolution of the data provides concentrations of the nucleotides or intercalating dyes detected Example Integrated System FIG. 2, Panels A, B, and C and FIG. 3 provide additional details regarding example integrated systems that are optionally used to practice the methods herein. As shown, body structure 202 has main channel 210 disposed therein. For example, particle array comprising a set of DNA template and primers is optionally flowed from pipettor channel 220 towards reservoir 214, e.g., by applying a vacuum at reservoir 214 (or another point in the system) or by applying appropriate voltage gradients. Reagents, e.g., nucleotides and polymerase, are optionally flowed into main channel 210 from reservoirs 208 and 204 or from pipettor channel 220. The templates incubate in main channel 210 with, e.g., polymerase and one or more nucleotides or nucleotide analogs. If an appropriate nucleotide, e.g., complementary to the template, is present, the polymerase adds the nucleotide to the primer strand of the nucleic acid, thus extending the double stranded region of the nucleic acid. A buffer or wash solution is optionally flowed from reservoir 208, 204, or pipettor channel 220 into main channel 210 to inactivate or remove any nucleotides that were not incorporated into the primer strand. Additional materials, such as buffer solutions, intercalating dyes, other sequencing reagents, and the like, as described above are optionally flowed into main channel 210. The added nucleotide remains attached to the primer strand and is detected, e.g., in main channel 210, e.g., at a particle retention area in the downstream end of the channel. Flow from these wells is optionally performed by modulating fluid pressure, or by electrokinetic approaches as described (or both). The arrangement of channels depicted in FIG. 2 is only one possible arrangement out of many which are appropriate and available for use in the present invention.

Samples and materials are optionally flowed from the enumerated wells or from a source external to the body structure. As depicted, the integrated system optionally includes pipettor channel 220, e.g., protruding from body 202, for accessing a source of materials external to the microfluidic system. Typically, the external source is a microtiter dish or other convenient storage medium. For example, as depicted in FIG. 3, pipettor channel 220 can access microwell plate 308, which includes sample materials, nucleotides, templates, primers, polymerase, particle arrays, intercalating dyes, and the like, in the wells of the plate.

Detector 310 is in sensory communication with channel 204, detecting signals resulting, e.g., from labeled nucleotides or nucleic acids. Detector 310 is optionally coupled to any of the channels or regions of the device where detection is desired. Detector 310 is operably linked to computer 304, which digitizes, stores, and manipulates signal information detected by detector 310, e.g., using any of the instructions described above, e.g., or any other instruction set, e.g., for determining concentration or identity.

Fluid direction system 302 controls voltage, pressure, or both, e.g., at the wells of the systems or through the channels of the system, or at vacuum couplings fluidly coupled to channel 210 or other channel described above. Optionally, as depicted, computer 304 controls fluid direction system 302. In one set of embodiments, computer 304 uses signal information to select further parameters for the microfluidic system. For example, upon detecting the addition or lack of addition of a nucleotide to a primer, the computer optionally directs addition of a different nucleotide into the system.

Kits

Generally, the microfluidic devices described herein are optionally packaged to include reagents for performing the device's preferred function. For example, the kits optionally include any of microfluidic devices described along with assay components, reagents, sample materials, particle sets, control materials, or the like. For example a kit for sequencing by synthesis with detection by intercalation typically includes an intercalating dye and a series of nucleotides, e.g., CTP, GTP, ATP, and TTP. A kit or sequencing by incorporation using 3'-blocking groups typically includes a series of nucleotide analogs, such as those of formulas (I) and (II) along with reagents for removing the 3'-blocking group, such s reducing agents and phosphatases. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

Kits also optionally include packaging materials or containers for holding microfluidic device, system or reagent elements.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system for sequencing a nucleic acid as set forth herein.

The use of a microfluidic system for sequencing by synthesis or incorporation as set forth herein.

The use of a microfluidic system for sequencing by photobleaching as set forth herein.

The use of a microfluidic system for sequencing by synthesis with detection of intercalating dyes as described herein.

A sequencing reaction utilizing any of the devices, methods, or nucleotide analogs described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were individually so denoted.

What is claimed is:

1. A method of sequencing a nucleic acid, the method comprising:
   (i) providing a nucleic acid template and a primer;
   (ii) incubating the nucleic acid template and primer with a polymerase and one or more fluorescently labeled nucleotides, thereby adding at least one of the one or more fluorescently labeled nucleotides to the primer, resulting in an extended primer;
   (iii) detecting the at least one fluorescently labeled nucleotide added to the primer;
   (iv) photobleaching the at least one or the one or more fluoroescently labeled nucleotides on the extended primer by applying a light pulse, wherein photobleaching destroys or reduces the fluorescence of the at least one of the one or more fluorescently labeled nucleotides to an acceptable level without removing the labeled nucleotide(s) from the extended primer.

2. The method of claim 1, wherein the nucleic acid template comprises DNA or RNA.

3. The method of claim 1, wherein the one or more fluorescently labeled nucleotides comprise one or more of: deoxyadenosine 5'-triphosphate, deoxyguanosine 5'-triphosphate, deoxycytidine 5'-triphosphate, deoxythymidine 5'-triphosphate, deoxyuridine 5'-triphosphate, adenosine 5'-triphosphate, guanosine 5'-triphosphate, cytidine 5'-triphosphate, uridine 5'-triphosphate, and an analog thereof.

4. The method of claim 1, wherein the one or more fluorescently labeled nucleotides comprise a series of four detectably different nucleotides, which four different nucleotides are selected from: deoxyadenosine 5'-triphosphate, deoxyguanosine 5'-triphosphate, deoxycytidine 5'-triphosphate, deoxythymidine 5'-triphosphate, deoxyuridine 5'-triphosphate, adenosine 5'-triphosphate, guanosine 5'-triphosphate, cytidine 5'-triphosphate, uridine 5'-triphosphate, and an analog thereof.

5. The method of claim 1, wherein incubating the nucleic acid template and the primer with the polymerase and the one or more fluorescently labeled nucleotides further comprises removing unincorporated fluorescently labeled nucleotides prior to photobleaching.

6. The method of claim 1, wherein step (ii) comprises incubating the nucleic acid template and the primer with a first nucleotide and wherein step (v) comprises repeating steps (ii) through (iv) at least a first time for at least a second nucleotide, a third nucleotide, and a fourth nucleotide.

7. The method of claim 6, wherein the first nucleotide, the second nucleotide, the third nucleotide, and the fourth nucleotide each comprise a different nucleotide.

8. The method of claim 7, wherein the different nucleotide is selected from: deoxyadenosine 5'-triphosphate, deoxyguanosine 5'-triphosphate, deoxycytidine 5'-triphosphate, deoxythymidine 5'-triphosphate, deoxyuridine 5'-triphosphate, adenosine 5'-triphosphate, guanosine 5'-triphosphate, cytidine 5'-triphosphate, uridine 5'-triphosphate, and an analog thereof.

9. The method of claim 1, wherein the detecting step and photobleaching step are carried out concurrently.

10. The method of claim 1, comprising applying the light pulse for about 20 seconds or less, about 10 seconds or less, about 2 seconds or less, about 1 second or less, or about 0.1 second or less.

11. The method of claim 1, wherein the light pulse has a wavelength equal to a wavelength of light absorbed by the at least one of the one or more fluorescently labeled nucleotides.

12. The method of claim 1, wherein the photobleaching step reduces the fluorescence of the extended primer to a background level.

13. The method of claim 1, wherein the photobleaching step reduces the fluorescence of the at least one of the one or more fluorescently labeled nucleotides to a background level.

14. The method of claim 1, wherein step (iii) comprises photobleaching the at least one or more fluorescently labeled nucleotides for about 20 seconds or less, about 10 seconds or less, about 2 seconds or less, about 1 second or less, or about 0.1 second or less.

15. The method of claim 1, the method further comprising detecting the at least one of the one or more fluorescently labeled nucleotides prior to or concurrent with photobleaching the at least one of the one or more fluorescently labeled nucleotides.

16. The method of claim 1, the method further comprising detecting the at least one of the one or more fluorescently labeled nucleotides by the photobleaching the at least one of the one or more fluorescently labeled nucleotides.

17. The method of claim 1, wherein the nucleic acid template comprises at least about 500 or more, about 1000 or more, about 2000 or more nucleotides, or about 10,000 or more nucleotides.

18. The method of claim 1, comprising sequencing a nucleic acid template with at least about 80%, at least about 90%, or at least about 95% accuracy, which nucleic acid template comprises at least about 500 or more, about 1000 or more, about 2000 or more, or about 10,000 or more nucleotides.

19. The method of claim 1, comprising performing steps (i) through (iv) in a microscale channel.

20. The method of claim 1, the method further comprising washing the microscale channel after step (ii), thereby removing or rendering unincorporable any unincorporated nucleotides from the microscale channel.

21. The method of claim 1, comprising providing a set of particles, which set of particles comprises one or more of: the nucleic acid template and the primer.

22. The method of claim 21 wherein the set of particles comprises an ordered array.

23. The method of claim 21, wherein the set of particles comprises about 1 or more particles, about 10 or more particles, about 100 or more particles, about 1000 or more particles, or about 10,000 or more particles.

24. The method of claim 21, wherein the set of particles comprises a set of beads, which beads are selected from: polymer beads, silica beads, ceramic beads, clay beads, glass beads, magnetic beads, metallic beads, paramagnetic beads, inorganic beads, and organic beads; and wherein the beads have a shape, which shape is selected from one or more of: spherical, helical, cylindrical, spheroid, irregular, rod shaped, cone shaped, cubic, and polyhedral.

25. The method of claim 21, comprising positioning the set of particles within a microscale channel.

26. The method of claim 21, wherein the incubating step comprises flowing the polymerase across the set of particles or flowing the set of particles through the polymerase.

* * * * *

UNITED STATES PATENT AND TRADEMARK OFFICE
CERTIFICATE OF CORRECTION

PATENT NO. : 6,613,513 B1
DATED : September 2, 2003
INVENTOR(S) : Parce et al.

It is certified that error appears in the above-identified patent and that said Letters Patent is hereby corrected as shown below:

Column 37,
Line 57, after "least one", please delete "or" and insert -- of --.
Line 63, after "primer", please insert -- ; and (v) repeating steps (ii) through (iv) thereby sequencing the nucleic acid --.

Column 38,
Line 52, please delete "(iii)" and insert -- (iv) --.

Column 39,
Line 10, please delete "(iv)" and insert -- (v) --.

Signed and Sealed this

Thirteenth Day of January, 2004

JON W. DUDAS
*Acting Director of the United States Patent and Trademark Office*